(12) United States Patent
Bierman

(10) Patent No.: US 11,839,735 B2
(45) Date of Patent: Dec. 12, 2023

(54) VASCULAR ACCESS DEVICE

(71) Applicant: Smiths Medical ASD, Inc., Plymouth, MN (US)

(72) Inventor: Steven F. Bierman, Del Mar, CA (US)

(73) Assignee: Smiths Medical ASD, Inc., Plymouth, MN (US)

( * ) Notice: Subject to any disclaimer, the term of this patent is extended or adjusted under 35 U.S.C. 154(b) by 101 days.

(21) Appl. No.: 16/598,173

(22) Filed: Oct. 10, 2019

(65) Prior Publication Data

US 2020/0038643 A1    Feb. 6, 2020

Related U.S. Application Data

(63) Continuation of application No. PCT/US2018/027377, filed on Apr. 12, 2018.

(60) Provisional application No. 62/485,797, filed on Apr. 14, 2017.

(51) Int. Cl.
| | | |
|---|---|---|
| A61M 39/02 | (2006.01) | |
| A61M 25/00 | (2006.01) | |
| A61M 25/06 | (2006.01) | |
| A61M 25/09 | (2006.01) | |
| A61M 29/00 | (2006.01) | |

(52) U.S. Cl.
CPC ........ *A61M 39/02* (2013.01); *A61M 25/0097* (2013.01); *A61M 25/0606* (2013.01); *A61M 25/09041* (2013.01); *A61M 29/00* (2013.01); *A61M 25/0668* (2013.01); *A61M 2039/0258* (2013.01); *A61M 2039/0273* (2013.01)

(58) Field of Classification Search
CPC .......... A61M 25/0097; A61M 25/0062; A61M 25/0668; A61M 2025/0681; A61M 29/00; A61M 39/22
See application file for complete search history.

(56) References Cited

U.S. PATENT DOCUMENTS

| | | | |
|---|---|---|---|
| 500,740 A | 7/1893 | Doyle | |
| 1,241,352 A * | 9/1917 | Doering et al. | .......... B67B 7/28 141/330 |
| 3,540,447 A | 11/1970 | Howe et al. | |
| 3,565,074 A | 2/1971 | Foti et al. | |
| 3,670,729 A | 6/1972 | Bennett et al. | |
| 4,052,989 A | 10/1977 | Kline | |
| 4,068,659 A | 1/1978 | Moorehead | |
| 4,079,738 A | 3/1978 | Dunn et al. | |

(Continued)

FOREIGN PATENT DOCUMENTS

| | | |
|---|---|---|
| EP | 0139091 | 5/1985 |
| EP | 0502714 | 11/1995 |

(Continued)

OTHER PUBLICATIONS

Arrow Trauma Products No. TRM-C 12/00 11M, Arrow International, 2000.

(Continued)

*Primary Examiner* — Scott J Medway
(74) *Attorney, Agent, or Firm* — BENESCH, FRIEDLANDER, COPLAN & ARONOFF LLP

(57) ABSTRACT

The device includes a dilator having a valve element configured to at least inhibit fluid flow through the dilator in a distal direction, while not inhibiting the passage of articles (e.g., a guidewire) through the dilator in a proximal direction.

20 Claims, 20 Drawing Sheets

(56) References Cited

U.S. PATENT DOCUMENTS

| | | | |
|---|---|---|---|
| 4,170,993 A | 10/1979 | Alvarez | |
| 4,205,675 A | 6/1980 | Vaillancourt | |
| 4,230,123 A | 10/1980 | Hawkins, Jr. | |
| 4,240,411 A * | 12/1980 | Hosono | A61B 1/12 |
| | | | D24/129 |
| 4,417,886 A | 11/1983 | Frankhouser et al. | |
| 4,430,081 A * | 2/1984 | Timmermans | A61M 39/0606 |
| | | | 251/149.1 |
| 4,525,157 A | 6/1985 | Vaillancourt | |
| 4,581,019 A | 4/1986 | Curelaru et al. | |
| 4,610,665 A | 9/1986 | Matsumoto et al. | |
| 4,629,450 A | 12/1986 | Susuki et al. | |
| 4,653,477 A * | 3/1987 | Akui | A61B 1/00137 |
| | | | 128/912 |
| 4,655,750 A | 4/1987 | Vaillancourt | |
| 4,661,300 A | 4/1987 | Daugherty | |
| 4,726,374 A * | 2/1988 | Bales | A61M 39/0613 |
| | | | 606/108 |
| 4,772,264 A | 9/1988 | Cragg | |
| 4,791,937 A | 12/1988 | Wang | |
| 4,850,960 A | 7/1989 | Grayzel | |
| 4,850,975 A | 7/1989 | Furukawa | |
| 4,861,341 A | 8/1989 | Woodburn | |
| 4,869,259 A | 9/1989 | Elkins | |
| 4,894,052 A | 1/1990 | Crawford | |
| 4,917,668 A * | 4/1990 | Haindl | F16L 37/38 |
| | | | 604/167.03 |
| 4,917,669 A | 4/1990 | Bonaldo | |
| 4,917,679 A | 4/1990 | Kronner | |
| 4,950,252 A | 8/1990 | Luther et al. | |
| 4,961,729 A | 10/1990 | Vaillancourt | |
| 4,963,306 A | 10/1990 | Weldon | |
| 4,978,334 A | 12/1990 | Toye et al. | |
| 5,044,401 A * | 9/1991 | Giesler | F16L 37/32 |
| | | | 137/614.03 |
| 5,049,136 A | 9/1991 | Johnson | |
| 5,059,186 A | 10/1991 | Yamamoto et al. | |
| 5,066,284 A | 11/1991 | Mersch et al. | |
| 5,067,945 A | 11/1991 | Ryan et al. | |
| 5,098,389 A | 3/1992 | Cappucci | |
| 5,102,394 A | 4/1992 | Lasaitis et al. | |
| 5,105,807 A | 4/1992 | Kahn et al. | |
| 5,108,374 A | 4/1992 | Lemieux | |
| 5,135,502 A | 8/1992 | Koenig, Jr. et al. | |
| 5,135,505 A | 8/1992 | Kaufman | |
| 5,167,636 A * | 12/1992 | Clement | A61M 39/0613 |
| | | | 604/167.03 |
| 5,167,637 A | 12/1992 | Okada et al. | |
| 5,171,218 A | 12/1992 | Fonger et al. | |
| 5,215,525 A | 6/1993 | Sturman | |
| 5,215,528 A | 6/1993 | Purdy et al. | |
| 5,242,410 A | 9/1993 | Melker | |
| 5,246,426 A | 9/1993 | Lewis et al. | |
| 5,250,038 A | 10/1993 | Melker et al. | |
| 5,279,590 A | 1/1994 | Sinko et al. | |
| 5,290,245 A | 3/1994 | Dennis | |
| 5,295,969 A | 3/1994 | Fischell | |
| 5,295,970 A | 3/1994 | Clinton et al. | |
| 5,306,253 A | 4/1994 | Brimhall | |
| 5,312,355 A | 5/1994 | Lee | |
| 5,312,363 A | 5/1994 | Ryan et al. | |
| 5,334,157 A | 8/1994 | Klein et al. | |
| 5,336,192 A * | 8/1994 | Palestrant | A61M 39/0613 |
| | | | 604/206 |
| 5,356,381 A * | 10/1994 | Ensminger | A61M 39/0208 |
| | | | 604/288.03 |
| 5,356,394 A | 10/1994 | Farley et al. | |
| 5,366,441 A | 11/1994 | Crawford | |
| 5,368,574 A * | 11/1994 | Antonacci | A61M 39/0606 |
| | | | 604/167.02 |
| 5,380,290 A | 1/1995 | Makower et al. | |
| 5,388,589 A | 2/1995 | Davis | |
| 5,397,311 A | 3/1995 | Walker et al. | |
| 5,403,283 A | 4/1995 | Luther | |
| 5,419,766 A | 5/1995 | Chang et al. | |
| 5,423,761 A | 6/1995 | Hein et al. | |
| 5,425,718 A | 6/1995 | Tay et al. | |
| 5,484,401 A * | 1/1996 | Rodriguez | A61M 1/84 |
| | | | 604/28 |
| 5,520,654 A | 5/1996 | Wahlberg | |
| 5,531,713 A | 7/1996 | Mastronardi et al. | |
| 5,542,932 A | 8/1996 | Daugherty | |
| 5,578,083 A | 11/1996 | Laguette et al. | |
| 5,589,120 A | 12/1996 | Khan et al. | |
| 5,657,963 A * | 8/1997 | Hinchliffe | A61M 39/06 |
| | | | 604/167.01 |
| 5,676,689 A | 10/1997 | Kensery et al. | |
| 5,688,249 A | 11/1997 | Chang et al. | |
| 5,704,914 A | 1/1998 | Stocking et al. | |
| 5,755,693 A | 5/1998 | Walker et al. | |
| 5,795,339 A | 8/1998 | Erskine | |
| 5,810,780 A | 9/1998 | Brimhall et al. | |
| 5,820,596 A | 10/1998 | Rosen et al. | |
| 5,820,606 A * | 10/1998 | Davis | A61B 17/3498 |
| | | | 604/164.11 |
| 5,827,202 A | 10/1998 | Miraki et al. | |
| 5,830,190 A | 11/1998 | Howell | |
| 5,833,662 A | 11/1998 | Stevens | |
| 5,853,393 A | 12/1998 | Bogert | |
| 5,858,002 A | 1/1999 | Jesch | |
| 5,858,007 A * | 1/1999 | Fagan | A61B 17/3462 |
| | | | 604/167.03 |
| 5,873,854 A | 2/1999 | Wolvek | |
| 5,885,253 A | 3/1999 | Liu | |
| 5,910,132 A | 6/1999 | Schultz | |
| 5,935,110 A | 8/1999 | Brimhall | |
| 5,951,518 A | 9/1999 | Licata et al. | |
| 6,046,143 A | 4/2000 | Khan et al. | |
| 6,066,117 A | 5/2000 | Fox et al. | |
| 6,074,377 A | 6/2000 | Sanfilippo | |
| 6,077,249 A | 6/2000 | Dittrich | |
| 6,080,141 A | 6/2000 | Castro et al. | |
| 6,083,207 A | 7/2000 | Heck | |
| 6,086,570 A * | 7/2000 | Aboul-Hosn | A61M 39/0606 |
| | | | 604/167.03 |
| 6,120,494 A | 9/2000 | Jonkman | |
| 6,159,182 A | 12/2000 | Davis | |
| 6,179,813 B1 | 1/2001 | Ballow et al. | |
| 6,277,100 B1 | 8/2001 | Raulerson | |
| 6,436,070 B1 | 8/2002 | Botich et al. | |
| 6,461,362 B1 | 10/2002 | Halseth et al. | |
| 6,524,277 B1 | 2/2003 | Chang | |
| 6,569,120 B1 | 5/2003 | Green et al. | |
| 6,607,511 B2 | 8/2003 | Halseth et al. | |
| 6,641,564 B1 | 11/2003 | Kraus | |
| 6,692,462 B2 | 2/2004 | Mackenzie et al. | |
| 6,712,789 B1 * | 3/2004 | Lange | A61M 39/06 |
| | | | 604/246 |
| 6,726,659 B1 | 4/2004 | Stocking et al. | |
| 6,783,516 B2 | 8/2004 | O'Heeron et al. | |
| 6,808,520 B1 | 10/2004 | Fourkas | |
| 6,942,671 B1 | 9/2005 | Smith | |
| 6,994,693 B2 | 2/2006 | Tal | |
| 7,001,396 B2 | 2/2006 | Glazier et al. | |
| 7,025,746 B2 | 4/2006 | Tal | |
| 7,056,304 B2 * | 6/2006 | Bacher | A61B 17/3498 |
| | | | 604/167.03 |
| 7,083,626 B2 | 8/2006 | Hart et al. | |
| 7,101,353 B2 | 9/2006 | Lui et al. | |
| 7,163,525 B2 | 1/2007 | Franer | |
| 7,192,433 B2 | 3/2007 | Osypka et al. | |
| 7,270,649 B2 | 9/2007 | Fitzgerald | |
| 7,322,964 B2 * | 1/2008 | Pajunk | A61B 17/3498 |
| | | | 604/246 |
| 7,350,656 B2 * | 4/2008 | Hidding | B67D 3/0032 |
| | | | 215/256 |
| 7,556,617 B2 | 7/2009 | Voorhees, Jr. et al. | |
| 7,717,878 B2 | 5/2010 | Smith | |
| 7,722,567 B2 | 5/2010 | Tal | |
| 7,744,569 B2 | 6/2010 | Smith | |
| 7,922,696 B2 | 4/2011 | Tal et al. | |
| 7,972,307 B2 | 7/2011 | Kraus et al. | |

(56) References Cited

U.S. PATENT DOCUMENTS

| | | |
|---|---|---|
| 7,993,305 B2 | 8/2011 | Ye et al. |
| 8,105,286 B2 * | 1/2012 | Anderson .......... A61M 25/0612 |
| | | 604/165.02 |
| 8,177,753 B2 * | 5/2012 | Vitullo ............... A61M 25/0113 |
| | | 604/167.03 |
| 8,192,402 B2 | 6/2012 | Anderson et al. |
| 8,202,251 B2 | 6/2012 | Bierman et al. |
| 8,827,958 B2 | 9/2014 | Bierman et al. |
| 9,101,737 B2 * | 8/2015 | King .................... A61M 25/06 |
| 9,233,230 B2 * | 1/2016 | Puhasmagi ....... A61M 25/0097 |
| 9,566,087 B2 | 2/2017 | Bierman et al. |
| 9,809,438 B2 * | 11/2017 | Broodryk ............... B67D 1/125 |
| 9,884,169 B2 | 2/2018 | Bierman et al. |
| 10,010,343 B2 | 7/2018 | Bierman et al. |
| 2002/0065373 A1 | 5/2002 | Krishnan |
| 2002/0072712 A1 | 6/2002 | Nool et al. |
| 2002/0087076 A1 | 7/2002 | Meguro et al. |
| 2004/0092879 A1 | 5/2004 | Kraus et al. |
| 2004/0171988 A1 | 9/2004 | Moretti |
| 2004/0243059 A1 | 12/2004 | Pajunk et al. |
| 2004/0267202 A1 | 12/2004 | Potter |
| 2005/0245875 A1 | 11/2005 | Restelli et al. |
| 2005/0267487 A1 * | 12/2005 | Christensen ....... A61B 17/3415 |
| | | 604/167.04 |
| 2006/0015039 A1 | 1/2006 | Cassidy et al. |
| 2006/0149293 A1 | 7/2006 | King et al. |
| 2007/0112302 A1 | 5/2007 | Yu |
| 2007/0123825 A1 | 5/2007 | King et al. |
| 2007/0293845 A1 * | 12/2007 | Leeflang ........... A61M 39/0606 |
| | | 604/523 |
| 2008/0004569 A1 | 1/2008 | McCrystle et al. |
| 2008/0097386 A1 * | 4/2008 | Osypka ............. A61M 25/0668 |
| | | 604/167.03 |
| 2008/0234728 A1 | 9/2008 | Starkksen |
| 2008/0300576 A1 * | 12/2008 | Vitullo .............. A61M 25/0097 |
| | | 604/523 |
| 2009/0018508 A1 | 1/2009 | Fisher et al. |
| 2009/0036843 A1 | 2/2009 | Erskine |
| 2009/0143737 A1 | 6/2009 | Kobayashi et al. |
| 2009/0177163 A1 | 7/2009 | King et al. |
| 2009/0221961 A1 | 9/2009 | Tal et al. |
| 2009/0227843 A1 | 9/2009 | Smith et al. |
| 2009/0259186 A1 | 10/2009 | Smith et al. |
| 2009/0312786 A1 | 12/2009 | Trask et al. |
| 2010/0042049 A1 | 2/2010 | Leeflang et al. |
| 2011/0021994 A1 | 1/2011 | Anderson et al. |
| 2011/0202006 A1 | 8/2011 | Bierman et al. |
| 2011/0218496 A1 * | 9/2011 | Bierman ........... A61M 25/0606 |
| | | 604/167.03 |
| 2011/0276002 A1 | 11/2011 | Bierman |
| 2011/0319838 A1 | 12/2011 | Goral |
| 2012/0065590 A1 * | 3/2012 | Bierman ................ A61M 25/01 |
| | | 604/164.05 |
| 2012/0136308 A1 | 5/2012 | Racz |
| 2012/0179144 A1 | 7/2012 | Carleo |
| 2013/0204226 A1 * | 8/2013 | Keyser .............. A61M 25/0097 |
| | | 604/506 |
| 2014/0128775 A1 * | 5/2014 | Andreae ............... A61B 5/1405 |
| | | 600/581 |
| 2014/0207069 A1 * | 7/2014 | Bierman ........... A61M 25/0668 |
| | | 604/167.03 |
| 2014/0221977 A1 | 8/2014 | Belson |
| 2014/0257042 A1 | 9/2014 | Lenker et al. |
| 2014/0275951 A1 * | 9/2014 | Millett ............... A61B 17/3423 |
| | | 600/407 |
| 2015/0126930 A1 | 5/2015 | Bierman et al. |
| 2018/0221628 A1 | 8/2018 | Bierman |
| 2018/0271558 A1 | 9/2018 | Bierman |

FOREIGN PATENT DOCUMENTS

| | | |
|---|---|---|
| EP | 0904023 | 3/1999 |
| JP | 05-312363 | 11/1993 |
| JP | 08-336593 | 12/1996 |
| JP | 2001-190682 | 7/2001 |
| JP | 2002-172174 | 6/2002 |
| JP | 06-0066117 | 3/2006 |
| JP | 2010-132608 | 6/2010 |
| JP | 2015-511149 A | 4/2015 |
| JP | 2016-512132 A | 4/2016 |
| KR | 10-2005-0027359 | 3/2005 |
| WO | WO 1998/00195 | 1/1998 |
| WO | WO 2003/041598 | 5/2003 |
| WO | WO 2003/057272 | 7/2003 |
| WO | WO 2004/000407 | 12/2003 |
| WO | WO 2011/162866 | 12/2011 |
| WO | WO 2012/117028 | 9/2012 |
| WO | WO 2014/130636 | 8/2014 |
| WO | WO 2016/176065 | 5/2017 |

OTHER PUBLICATIONS

International Search Report and Written Opinion in PCT/US2018/027377 dated Jun. 20, 2018 in 22 pages.

Photos of a peripheral emergency infusion device Applicant believes to be produced by Arrow International Inc., Jul. 20, 2011.

Photos of a splittable catheter design, Jul. 20, 2011.

Photos of an infusion device Applicant believes to be produced by B. Braun Medical Inc., Jul. 20, 2011.

Office Action dated Dec. 16, 2021 for Japanese Application No. 2019-555434, 8 pages.

Office Action dated May 22, 2023 for Japanese Application No. 2022-076398, 8 pages.

* cited by examiner

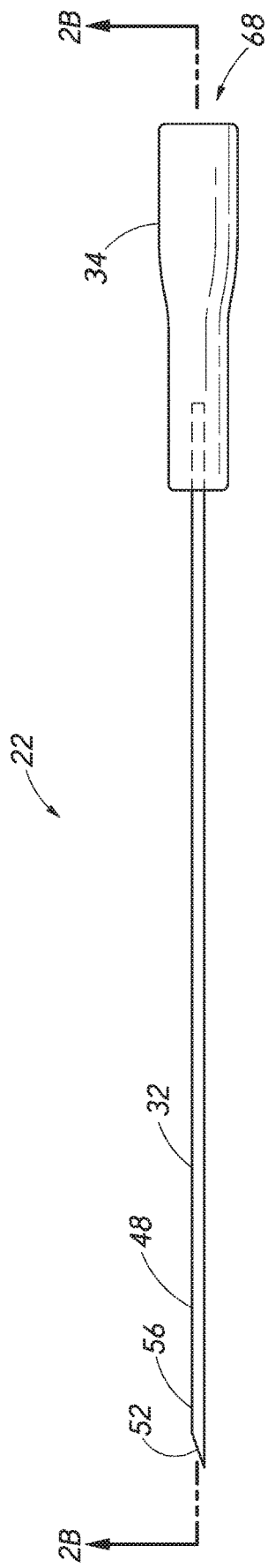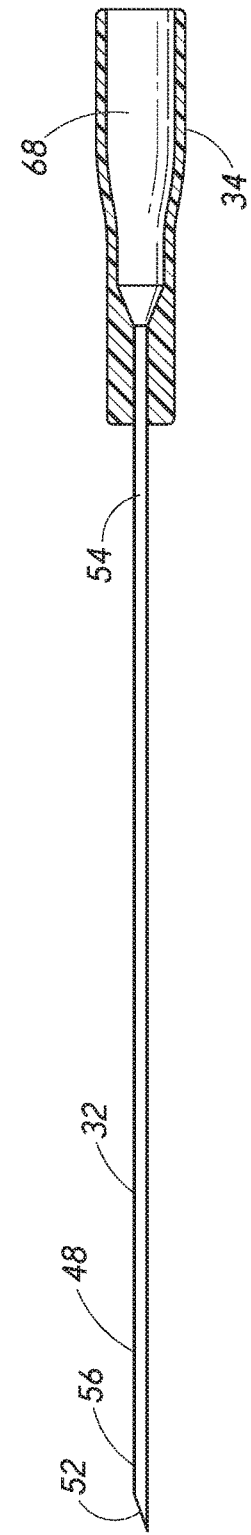
FIG. 2A
FIG. 2B

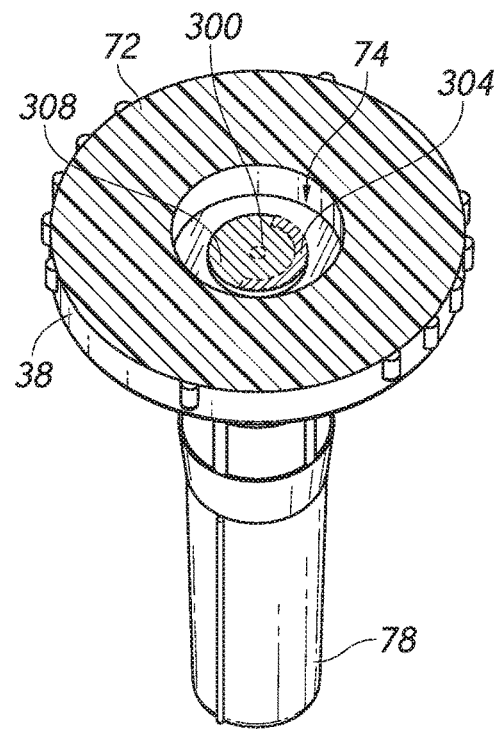
FIG. 4A
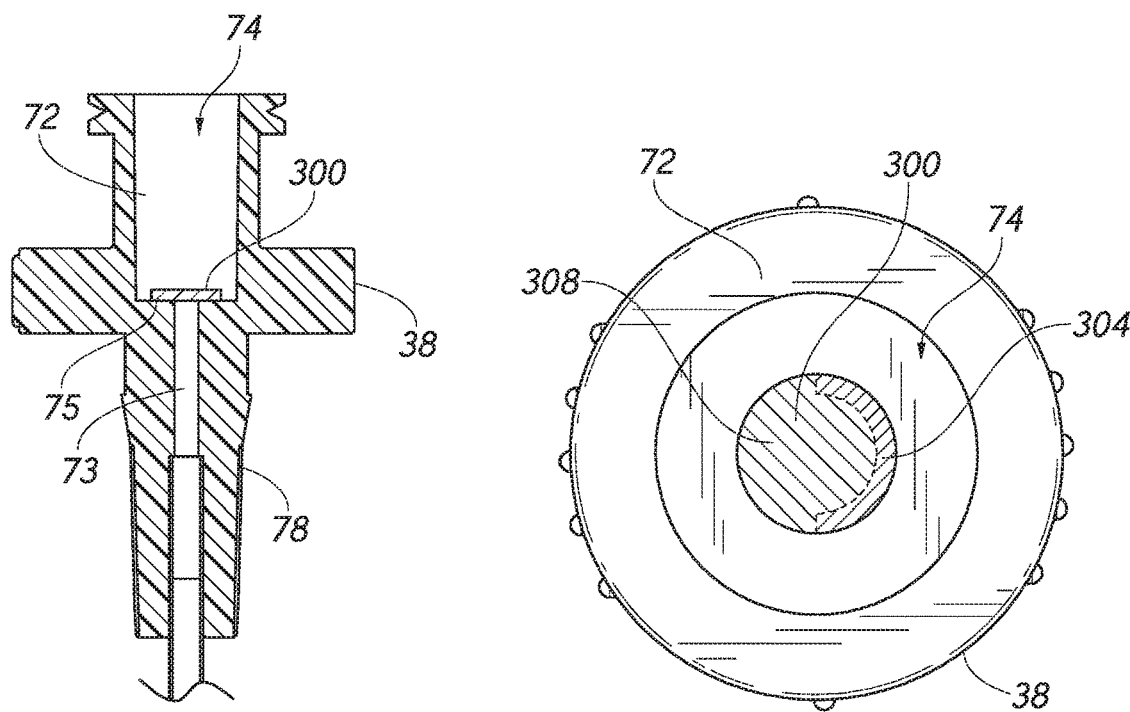
FIG. 4B
FIG. 4C

VASCULAR ACCESS DEVICE

INCORPORATION BY REFERENCE

This application is a continuation application of PCT Patent Application No. PCT/US2018/027377, filed Apr. 12, 2018, which claims priority to U.S. Provisional Patent Application No. 62/485,797, filed on Apr. 14, 2017. The entire contents of each of which are hereby incorporated by reference herein in their entireties, forming part of the present disclosure. Any feature, structure, material, method, or step that is described and/or illustrated in any embodiment in the foregoing provisional patent application can be used with or instead of any feature, structure, material, method, or step that is described in the following paragraphs of this specification and/or illustrated in the accompanying drawings.

BACKGROUND

Field

The present disclosure is generally directed to access devices for introducing and/or delivering a medical article (such as, for example, a catheter, cannula, sheath, etc.) into a body space, such as, for example, an artery, vein, vessel, body cavity, or drainage site, and more specifically, to devices which include a valve member for substantially sealing one or more fluid pathways.

Description of the Related Art

Various medical devices, for example, catheters, cannulas, sheaths, etc., are often introduced into a patient, for example, in an artery, vein, body cavity, or drainage site, to deliver fluids to or withdraw fluids from the patient. For example, a catheter or vascular sheath can be introduced into a patient's blood vessel using the Seldinger or a modified Seldinger technique. These techniques involve inserting an access needle into the patient's blood vessel and then inserting a guidewire through the needle and into the vessel. A dilator and sheath in combination or separately are inserted over the guidewire through tissue into the vessel. The needle can be removed before or after inserting the dilator and sheath. The dilator and guidewire are then removed and discarded. The sheath can be left in the vessel, for example, to deliver medical fluids to the patient, or a catheter or other medical article can be inserted through the sheath into the vessel to a desired location.

Various access devices for performing the Seldinger or a modified Seldinger technique are known. Some access devices provide the needle, dilator, and/or sheath coaxially disposed about one another. Some such devices provide mechanisms for confirming vascular access.

SUMMARY

The access devices described herein advantageously provide improved mechanisms for safely achieving medical device placement within the vasculature. Without limiting the scope of this disclosure, its more prominent features will be discussed briefly. After considering this discussion, and particularly after reading the Detailed Description section below in combination with this section, one will understand how the features and aspects of these embodiments provide several advantages over prior access devices.

One aspect is an access device for placing a medical article within a body space. The access device includes a dilator having a hub and an elongated dilator body extending from the hub defining an inner cavity having a distal cavity portion and a proximal cavity portion. The access device further includes a valve element having an open position and a closed position, the valve element comprising an attachment portion configured to be supported by the dilator hub, and a sealing portion extending radially inwardly from a side of the inner cavity, the sealing portion being biased toward the closed position. The valve element can be configured to inhibit fluid flow between the distal cavity portion and the proximal cavity portion when the valve element is in the closed position. The valve element can permit movement of a guidewire through the dilator hub in a distal proximal direction relative to the dilator.

The access device may comprise one or more of the following features: the valve element can be at least partially disposed between the distal portion of the inner cavity and the proximal portion of the inner cavity; the sealing portion can comprise a first sealing surface, the dilator hub can comprise a second sealing surface, and the first sealing surface can be against the second sealing surface to substantially seal the distal cavity portion from the proximal cavity portion when the valve element is in the closed position; at least one of the first sealing surface and the second sealing surface can extend entirely around an inner perimeter of the inner cavity; the sealing portion can comprise a raised portion; the raised portion can extend within the distal portion of the inner cavity when the valve element is in the closed position; the raised portion can comprise a substantially dome-like shape; the valve element can comprise a fold line along which the sealing portion and the attachment portion can bend with respect to each other; the valve element can comprise a flexible material with properties that reduce the likelihood of cold-setting when held in a flexed position for extended periods of time; movement of the guidewire in a proximal direction relative to the dilator can be inhibited when the valve element is in the closed position; the access device can comprise a sheath disposed about the dilator.

Another aspect is an access device for placing a medical article within a body space. The access device includes a dilator having a hub and an elongated dilator body extending from the hub defining an inner cavity having a distal cavity portion and a proximal cavity portion. The access device further includes a sheath coaxially disposed about the dilator and a valve element comprising an attachment portion being supported within the inner cavity, and a sealing portion extending into the inner cavity, the sealing portion comprising a first sealing surface, wherein the first seal surface is biased toward a first position against a second sealing surface on at least one of the dilator body and the dilator hub to substantially seal to least a portion of the inner cavity from the dilator body, and wherein the sealing portion is movable from the first position to a second position when at least one of a needle and a guidewire is extended through the inner cavity.

The access device may comprise one or more of the following features: the valve element can be at least partially disposed between a distal portion of the inner cavity and a proximal portion of the inner cavity; at least one of the first sealing surface and the second sealing surface can extend entirely around an inner perimeter of the inner cavity; the sealing portion can comprise a raised portion; the raised portion can extend within the dilator body when the valve element is in the first position; the raised portion can comprise a substantially dome-like shape; the valve element can comprise a fold line along which the sealing portion and the attachment portion can bend with respect to each other; the valve element can comprise a flexible material with properties that reduce the likelihood of cold-setting when held in a flexed position for extended periods of time; movement of at least one of the needle and the guidewire in a proximal direction relative to the dilator can be inhibited when the valve element is in the closed position.

One aspect is a method of providing an access device for placing a medical article within a body space. The method includes providing a dilator having a hub and an elongated dilator body extending from the hub defining an inner cavity having a distal cavity portion and a proximal cavity portion. The dilator can further include a valve element comprising an attachment portion being supported within the inner cavity and a sealing portion extending into the inner cavity, the sealing portion comprising a first sealing surface, wherein the first seal surface is biased toward a first position against a second sealing surface on at least one of the dilator body and the dilator hub to substantially seal to least a portion of the inner cavity from the dilator body, and wherein the sealing portion is movable from the first position to a second position when at least one of a needle and a guidewire is extended through the inner cavity. The method can further include providing a sheath configured to be coaxially disposed about the dilator.

The access device may comprise one or more of the following features: the valve element can be at least partially disposed between a distal portion of the inner cavity and a proximal portion of the inner cavity; at least one of the first sealing surface and the second sealing surface can extend entirely around an inner perimeter of the inner cavity; the sealing portion can comprise a raised portion; the raised portion can extend within the dilator body when the valve element is in the first position; the raised portion can comprise a substantially dome-like shape; the valve element can comprise a fold line along which the sealing portion and the attachment portion can bend with respect to each other; the valve element can comprise a flexible material with properties that reduce the likelihood of cold-setting when held in a flexed position for extended periods of time; movement of at least one of the needle and the guidewire in a proximal direction relative to the dilator can be inhibited when the valve element is in the closed position.

The method can further include providing the access device comprising one or more of the following features: the valve element can be at least partially disposed between a distal portion of the inner cavity and a proximal portion of the inner cavity; at least one of the first sealing surface and the second sealing surface can extend entirely around an inner perimeter of the inner cavity; the sealing portion can comprise a raised portion; the raised portion can extend within the dilator body when the valve element is in the first position; the raised portion can comprise a substantially dome-like shape; the valve element can comprise a fold line along which the sealing portion and the attachment portion can bend with respect to each other; the valve element can comprise a flexible material with properties that reduce the likelihood of cold-setting when held in a flexed position for extended periods of time; movement of at least one of the needle and the guidewire in a proximal direction relative to the dilator can be inhibited when the valve element is in the closed position.

These and other aspects of the present invention will become readily apparent to those skilled in the art from the following detailed description of the disclosed embodiments, which refers to the attached figures. The invention is not limited, however, to the particular embodiments that are disclosed.

BRIEF DESCRIPTION OF THE DRAWINGS

The foregoing and other features, aspects, and advantages of the embodiments of the invention are described in detail below with reference to the drawings of various embodiments, which are intended to illustrate and not to limit the embodiments of the invention. The drawings comprise the following figures in which:

FIG. 2A is side view of a needle which can be employed to facilitate insertion of the guidewire of FIG. 1 into a patient.

FIG. 2B is a side cross-sectional view of the needle of FIG. 2A taken along line 2B-2B.

FIG. 4A is an enlarged perspective view of a portion of the dilator of FIG. 3A looking in the distal direction. The dilator includes an inner cavity housing the valve element.

FIG. 4B is an enlarged side cross-sectional view of the dilator of FIG. 3A taken along line 4B-4B of FIG. 3B.

FIG. 4C is an end view of the dilator of FIG. 4A looking in a distal direction.

DETAILED DESCRIPTION

Figure 1:
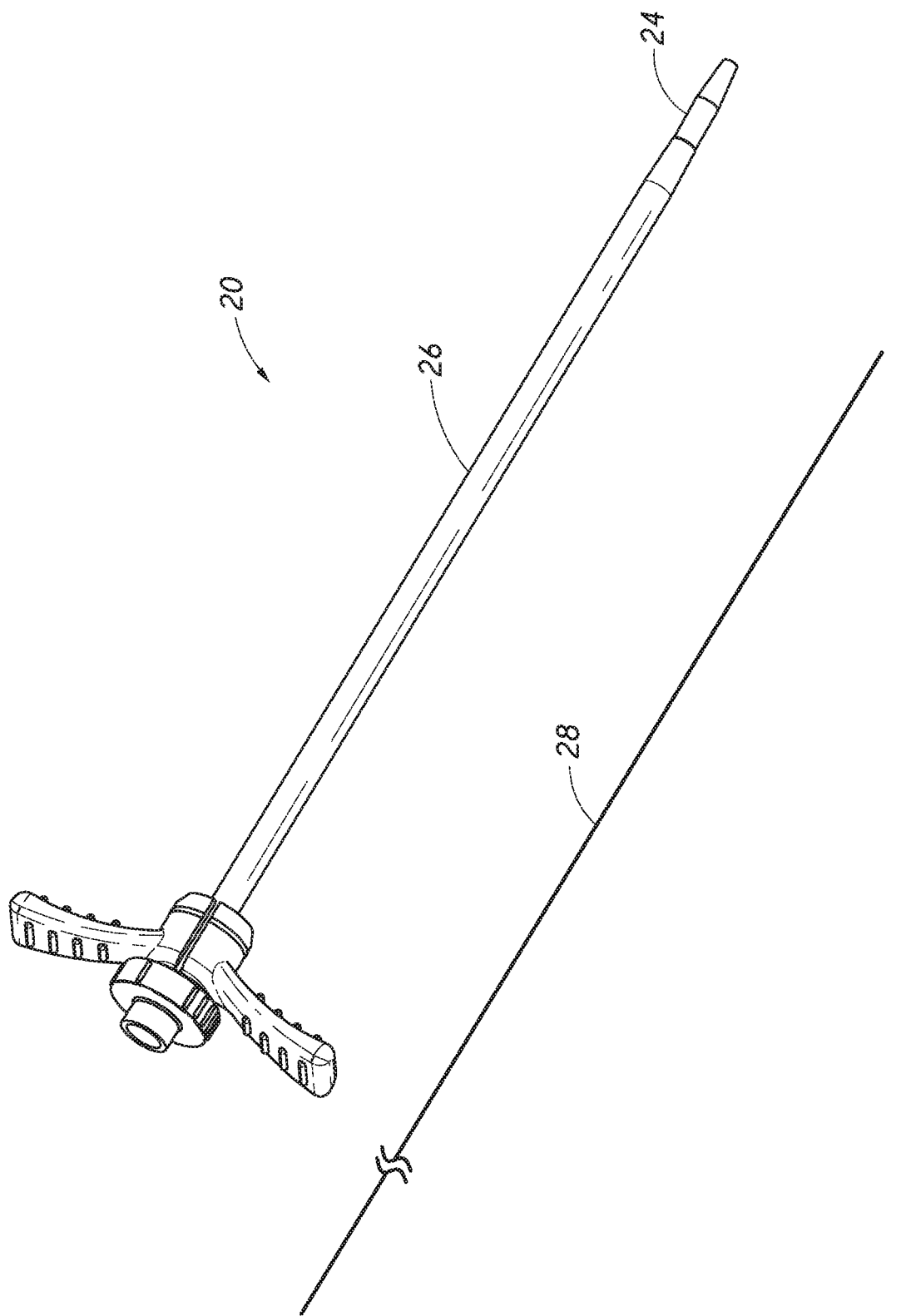
FIG. 1 is a perspective view of an embodiment of an access device including a dilator coaxially aligned with a sheath. A guidewire is also shown.

In various circumstances a physician may wish to introduce a catheter or sheath into a space within a patient's body, for example, a blood vessel or drainage site, to introduce fluids to the space or remove fluids from the space. Various access devices are known in the art. Examples of an improved access device are described in U.S. application Ser. No. 14/207,120, now U.S. Pat. No. 9,566,087, entitled "VASCULAR ACCESS DEVICE," filed Mar. 12, 2014, the entire contents of which is incorporated by reference herein and forms part of this specification. FIGS. 1A and 1B of U.S. Pat. No. 9,566,087 illustrate an access device 20 that can be used, for example, in performing the Seldinger or a modified Seldinger technique to introduce a catheter or sheath to a patient's blood vessel. While the access device is described herein in the context of vascular access, the access device also can be used to access and place a medical article (e.g., catheter or sheath) into other locations within a patient's body (e.g., a drainage site) and for other purposes (e.g., for draining an abscess).

The present disclosure of the access device is disclosed in the context of placing an exemplary single-piece, tubular medical article into a body space within a patient. Once placed, the tubular article can then be used to receive other medical articles (e.g., catheters, guidewires, etc.) to provide access into the body space and/or be used to provide a passage way for introducing fluids into the body space or removing (e.g., draining) fluids from the body space. In the illustrated embodiment, the tubular medical article is a sheath or catheter that is configured primarily to provide a fluid passage into a vein. The principles of the present invention, however, are not limited to the placement of single piece sheaths or catheters, or to the subsequent insertion of a medical article via the sheath or catheter. Instead, it will be understood in light of the present disclosure that the access device disclosed herein also can be successfully utilized in connection with placing one or more other types of medical articles, including other types of sheaths, fluid drainage and delivery tubes, and single or multi-lumen catheters directly in the patient or indirectly via another medical article.

For example, but without limitation, the access devices disclosed herein can also be configured to directly or indirectly place central venous catheters, peripherally inserted central catheters, hemodialysis catheters, surgical drainage tubes, tear-away sheaths, multi-piece sheaths, PICC lines, IV lines, scopes, as well as electrical conduit for wires or cables connected to external or implanted electronic devices or sensors. As explained above, the medical articles listed above may be directly placed in the patient via the dilator, needle, and guidewire of the access device or subsequently placed within the patient via a medical article that was placed within the patient via the dilator, needle, and guidewire of the access device.

Further, the embodiments disclosed herein are not limited to co-axial insertion of a single medical article. For example, two catheters may be inserted in the patient via an inserted sheath or a second catheter may be inserted in the patient via an inserted first catheter. Further, in addition to providing a conduit into the vessel or other body space, the medical article inserted via the dilator, needle, and guidewire can form a lumen that is in addition to the lumen(s) of the subsequently inserted medical article. One skilled in the art can also find additional applications for the devices and systems disclosed herein. Thus, the illustration and description of the access device in connection with a sheath (e.g., for micro puncture applications) is merely exemplary of one possible application of the access device.

FIG. 1 is a perspective view of an embodiment of an access device 20 that includes a dilator 24 coaxially aligned with a sheath 26. A guidewire 28 is also shown. The components of the access device 20 illustrated in FIG. 1 include a dilator 24 and a sheath 26. In the illustrated embodiment, the access device 20 also includes the guidewire 28. The sheath 26 can be coaxially mounted on the dilator 24. The telescoping nature of the access device's components can also be accomplished by arranging the components with their axes arranged substantially parallel rather than coaxially (e.g., a monorail-type design).

Each of these components includes a luminal fitting at a terminal end or transition (e.g., a hub) and elongated structure that extends from the fitting. Thus, in the illustrated embodiment shown in FIGS. 3A and 8B, the dilator 24 includes a dilator shaft 36 that extends distally from a dilator hub 38, and the sheath 26 includes a sheath body 40 that extends distally from a sheath hub 42. In certain embodiments, the guidewire 28 includes a guidewire hub or cap.

FIG. 2A is side view of a needle 22 which can be employed to facilitate insertion of the guidewire 28 from FIG. 1 into a patient. FIG. 2B is a side cross-sectional view of the needle 22 of the embodiment depicted in FIG. 2A taken along line 2B-2B. The needle 22 includes a needle body 32 and a needle hub 34. As best seen in FIG. 2B, the needle hub 34 is disposed on a proximal end of the needle body 32. The needle body 32 terminates at a distal end near a distal portion 48 of the needle 22, and the needle hub 34 lies at a proximal portion of the needle 22.

The needle body 32 has an elongated tubular shape having a circular, constant-diameter interior bore 54 and a circular, constant-diameter exterior surface. In other embodiments, however, the needle body 32 can have other bore and exterior shapes (such as, for example, but without limitation, an oval cross-sectional shape). The interior or exterior of the needle 22 can also include grooves or channels. The grooves or channels may guide fluids within the needle bore either around or to certain structures of the needle 22 or within the needle 22 (e.g., around the guidewire 28). In some embodiments, the grooves or channels may assist in maintaining a desired orientation of the needle 22 with respect to the dilator 24.

The needle body 32 has a sufficiently long length to access a targeted subcutaneous body space and has a sufficient gauge size to withstand the insertion forces when accessing the body space without causing undue trauma. For many applications, the needle body 32 can have a length between 3-20 cm (e.g., between 3-10 cm). For example, to access a body space (e.g., a vessel) in the thorax of an adult human, the needle body 32 has a length of 7 cm or greater, a length of 9 cm or greater, and/or a length of 9 to 10 cm. The size of the needle 22 can be 18 gauge or smaller (e.g., between 18-28 gauge or between 18-26 gauge for micro-puncture applications (peripheral IVs)). For applications with a neonate, the length and gauge of the needle body 32 should be significantly shorter and smaller, for example between 3-4 cm and between 26-28 gauge. The needle body 32 can have a bevel tip 52 disposed on the distal portion 48.

As explained below in greater detail, the guidewire 28 is introduced through a hollow portion 68 of the needle hub 34, through the needle body 32, and into a punctured vessel. After removing the needle 22 from the patient, the remaining guidewire 28 allows the healthcare provider to guide the dilator 24 and sheath 26 into the vessel.

Figure 3A:
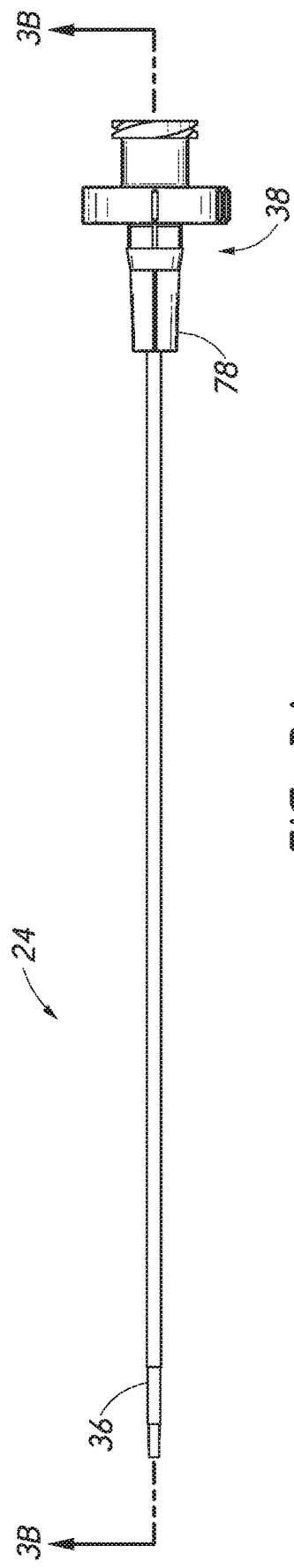
FIG. 3A is a side view of a dilator including a valve element.
Figure 3B:
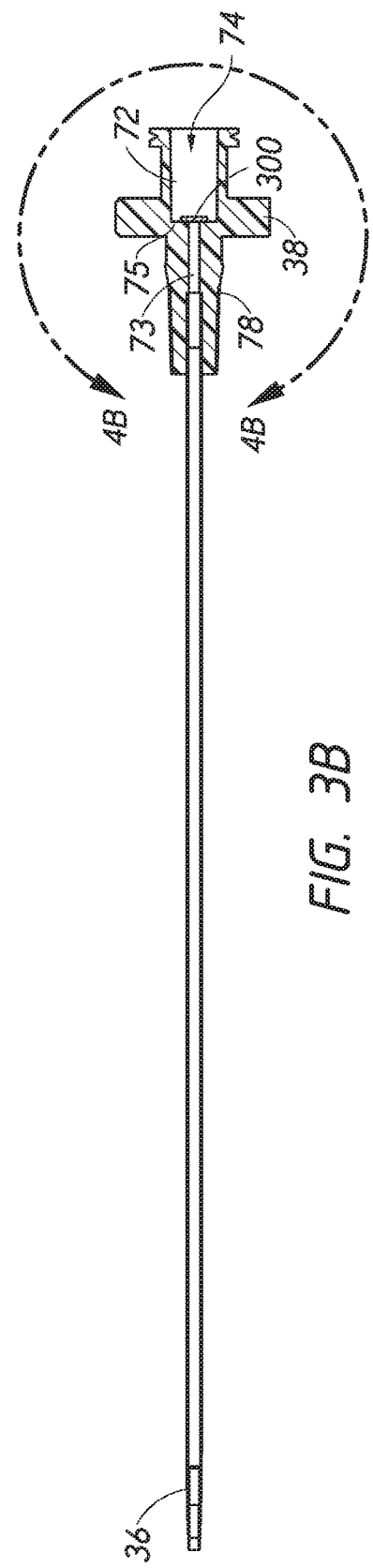
FIG. 3B is a side cross-sectional view of the dilator of FIG. 3A taken along the lines 3B-3B.

FIG. 3A is a plan view of a dilator 24 that can be used with the access device 20 of FIG. 1 and includes a valve element 300 (not shown in FIG. 3A). FIG. 3B is a side cross-sectional view taken along the lines 3B-3B in FIG. 3A showing the valve element 300. The illustrated dilator 24 comprises a dilator shaft 36, a dilator hub 38, and an inner cavity 74 including a distal portion 73 and a proximal portion 72.

FIG. 4A is an enlarged perspective view of a portion of the dilator hub 38 illustrated in FIG. 3A when the valve element 300 is in a closed position. FIG. 4B is a side cross-sectional view of the dilator hub 38 depicted in FIG. 3B circled by line 4B-4B. FIG. 4C is an end view of the dilator hub 38 depicted in FIG. 3A looking in a distal direction. The dilator 24 includes an inner cavity 74. In certain embodiments, the inner cavity 74 is configured to house the valve element 300, as described herein. The inner cavity 74 can be sized and shaped so as to allow the valve element 300 to be housed in the dilator hub 38. However, the valve element 300 need not reside within the dilator hub 38. In certain embodiments, the valve element 300 resides on a proximal end (e.g., on top) of the dilator 24 or outside the dilator 24 as long as the guidewire 28 passes along the valve element 300.

With continued reference to FIGS. 3A-4C, the valve element 300 can be configured to substantially seal at least a portion of the inner cavity 74 of the dilator hub 38 or other passage in the dilator through which the guidewire can pass. Valve element 300, in some instances, can be positioned between a proximal portion 72 of inner cavity 74 and a distal portion 73 of inner cavity 74, such that the valve element 300 can be configured to substantially seal the proximal portion 72 from the distal portion 73. Portions 72, 73 can comprise any of a variety of sizes and shapes and are shown with an approximately circular cross-sectional shape for illustrative purposes only. In some embodiments, distal portion 73 of inner cavity 74 comprises at least a region having a cross-sectional area that is less than proximal portion 72 to facilitate sealing of valve element 300 against distal portion 73. In this arrangement, the valve element 300 can be configured as a one-way valve structure by substantially inhibiting fluid flow through the inner cavity 74 in a distal direction, while not substantially inhibiting the passage of articles (e.g. guidewire 28 as shown in FIGS. 5-6B) through the inner cavity 74 in a proximal direction.

The valve element 300, as illustrated, includes a sheath or disc that is configured to interact with at least a portion of the dilator hub 38 (e.g., sealing surface 75 described herein), as shown in FIGS. 3B-6B. The valve element 300 can be positioned over, against, or around any portion of the dilator hub 38 to seal at least a portion of the inner cavity 74. The valve element 300 can be made of a single unitary body.

Figure 5:
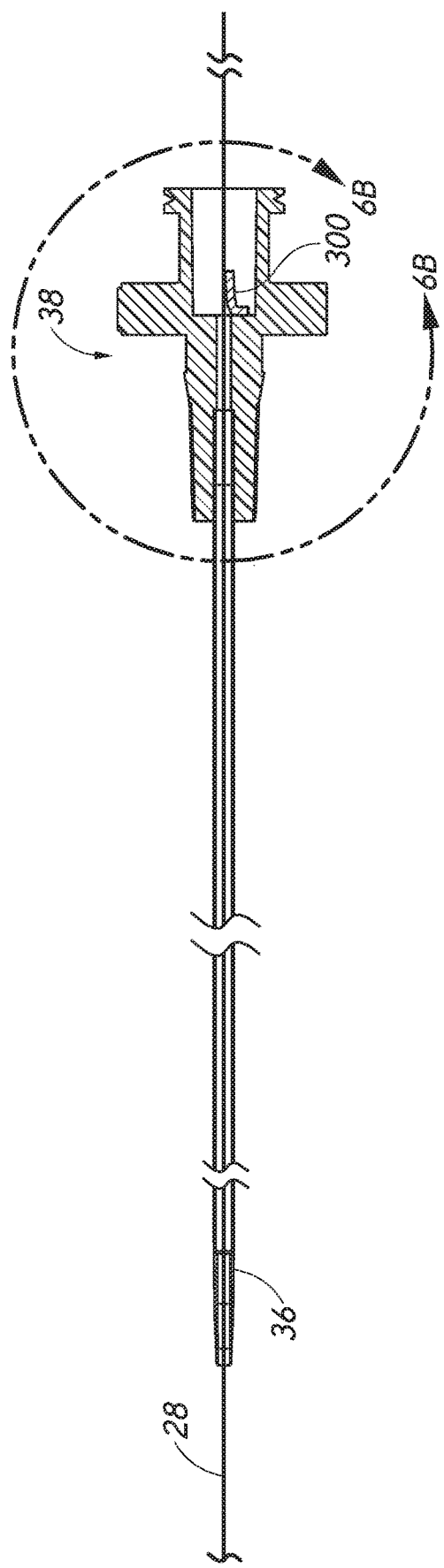
FIG. 5 is a side cross-sectional view of the dilator of FIG. 3A with a guidewire extending through the dilator.
Figure 6A:
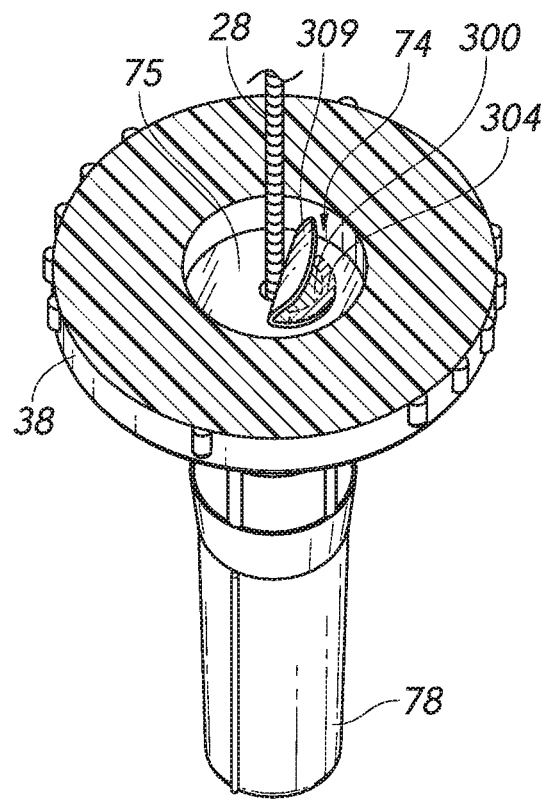
FIG. 6A is an enlarged perspective view of a portion of the dilator of FIG. 5A looking in the distal direction.
Figure 6B:
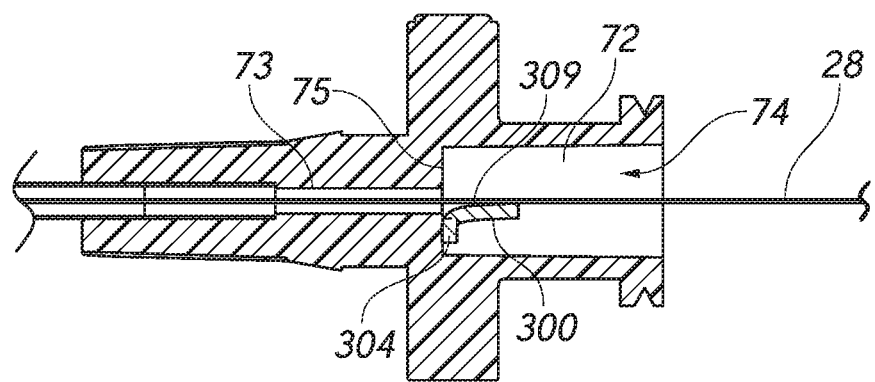
FIG. 6B is an enlarged side cross-sectional view of the dilator of FIG. 5 taken along line 6B-6B.

As shown in FIGS. 3B and 5, respectively, the valve element may have a first configuration and a second configuration (e.g., a closed position and an open position, respectively). Valve element 300 can be adapted to flex or move between the closed or substantially sealed position (e.g., as shown in FIGS. 3B-4C) and the open or unsealed position (e.g., as shown in FIGS. 5-6B) through flexation, flexing, or flexing of a sealing portion 308 of the valve element 300. Valve element 300 can move between the open and closed positions due to the passage of a device (e.g. guidewire 28) through the dilator hub 338 and/or through operation by a user. In some embodiments, the valve element 300 can comprise an elastomeric material and/or flexible structure capable of deformation or movement as a device (e.g., a guidewire) abuts against and extends through the valve element 300.

As illustrated in FIG. 3B, when the valve element 300 is in the first configuration (e.g., the closed position), the valve element 300 may be placed along a portion of the dilator hub 38. For example, when in the closed position, a sealing surface 309 of the valve element 300 that is located on a distal surface of the sealing portion 308 can contact or otherwise engage with a corresponding sealing surface 75 of the dilator hub 38 that is located on a proximal-facing surface of the dilator hub 38. The interaction of the respective sealing surfaces 309, 75 can be sufficient to inhibit passage of fluids through the inner cavity 74 in the proximal and/or distal directions.

Valve element 300 can include an attachment portion 304 supporting the sealing portion 308. The attachment portion 304 can be supported by a portion of the dilator hub 38, such that the sealing portion 308 can extend (e.g., radially inwardly) into the inner cavity 74 and substantially seal an aperture within the inner cavity 74. An attachment portion 304 of the valve element 300 can comprise any of a variety of materials with sufficient rigidity to support sealing portion 308. The material may comprise sufficient flexibility to allow sealing portion 308 to flex or move between the open and closed positions, as described herein. The attachment portion 304 also can comprise a bio-compatible metal or plastic, or various composites or combinations thereof. Attachment portion 304 can comprise a material with reduced susceptibility to cold-setting. For example, in some applications, a medical article can be extended through inner cavity 74 with the valve element 300 in an open position and can be packaged together for a period of time within the dilator 24, without compromising the valve features (e.g., its flexibility and ability to seal inner cavity 74 when in a closed position). For example, the access device can be packaged pre-assembled with the guidewire 28 coaxially disposed within the dilator 24.

The valve element 300 can be sized and configured to extend along and enclose any portion and/or length of the inner cavity 74 of the dilator hub 38 to substantially seal the proximal portion 72 of the inner cavity 74 from the distal portion 73 of the inner cavity 74. For example, the valve element 300 can be configured to be positioned over and enclose the distal portion 73 of the inner cavity 74 at a distal end of the proximal portion 72 of the inner cavity 74. The valve element 300 can be configured such that the attachment portion 304 of the valve element 300 is positioned along a first portion of the dilator hub 38 and the sealing portion 308 of the valve element 300 is positioned along a second portion of the dilator hub 38 to substantially enclose the distal portion 73 of the inner cavity 74. The valve element 300 can be configured to adhere to the dilator hub 38 when in the open position and/or the close position. In some embodiments, as described herein, the attachment portion 304 of the valve element 300 can comprise an adhesive to adhere at least to the dilator hub 38.

The valve element 300 may comprise a restorative force biasing the valve element 300 towards a closed position. Notably, the restorative force can cause the sealing surface 309 to press against the sealing surface 75. In some embodiments, this mechanism can be sufficiently resilient to withstand pressures associated with human blood vessels to inhibit blood from passing through the valve element 300 in a proximal direction when the valve element 300 is closed. As such, the mechanism advantageously inhibits a loss of blood through the valve element 300 when closed. This mechanism may, in some instances, be sufficient to maintain the placement of a device (e.g., a guidewire) within the dilator hub 38 when the device is inserted thought the dilator 24 (as shown in FIG. 5). For example, the restorative force can cause the valve element 300 to engage the device to inhibit unintentional movement of the device relative to the dilator 28.

In some embodiments, the valve element 300 is configured such that the sealing surface 309 of the sealing portion 308 is preloaded against sealing surface 75 of the dilator hub 38 such that valve element 300 is preloaded in the closed position, as described herein. This biasing can enhance the above-described inhibition of passage of matter in the distal and/or proximal directions. The biasing can help the valve element 300 inhibit passage of matter, such as the flow of fluid (e.g., blood or air) or passage of a device, in a proximal and/or distal directions (e.g., longitudinally) within inner cavity 74. For example, the bias towards the closed position can be strong enough to resist a force (or cracking pressure) in the proximal and/or direction to open the valve element 300. In some embodiments, the preload or bias of valve element 300 can be sufficient to prevent gas from being drawn distally through the inner cavity 74 and into a patient due to, for example, negative pressure created by a human during a normal pulse. Notably, drawing gas into a blood vessel can cause serious health effects such as an embolism.

FIG. 5 is a side cross-sectional view similar to FIG. 3B with the dilator 24 and the sheath 26 threaded over a guidewire 28 until the guidewire 28 abuts against and extends past the valve element 300 to cause the valve element 300 to move from the closed position to the open position. FIG. 6A is an enlarged perspective view of a portion of the dilator hub 38 illustrated in FIG. 5 looking in the distal direction when the valve element is in an open position. FIG. 6B is a side cross-sectional view of the dilator hub 38 depicted in FIG. 5 circled by line 6B-6B. In the illustrated embodiments, the dilator 28 has slid in a distal direction relative to the guidewire 28 until the valve element 300 engages the guidewire 28. The sealing surface 309 of the valve element 300 can engage with an external surface of the guidewire 28 as the guidewire 28 passes through the dilator hub 38 and extends past the valve element 300.

As discussed herein, the valve element 300 can be biased towards a closed position. The degree of bias of the valve element 300 towards the closed position can be selected so that the guidewire 28 is permitted to slide easily through the valve element 300 when the dilator 24 is threaded over the guidewire 28. In certain embodiments, as the guidewire 28 is initially threaded through the dilator hub 38, the valve element 300 abuts against the outer surface of the guidewire 28 so as to press against the guidewire 28. The biasing force, in some instances, may be insufficient to meaningfully interfere with the of the guidewire 28 being threaded through the valve element 300. That is, the biasing force of the valve element 300 on the guidewire 28 can still permit movement of the guidewire 28 relative to the valve element 300. For example, the valve element 300 may not sufficiently resist passage of the guidewire 28 through the dilator hub 38 in a proximal direction relative to the dilator hub 38.

The sealing portion 308 may include a raised portion, such as substantially dome-shaped portion adjacent to and/or along at least a portion of the sealing surface 309. The dome-shaped portion can prevent or reduce the likelihood of contact between the sealing surface 309 and a device (e.g. the guidewire 28), when the device is passing and/or extending through inner cavity 74. For example, if the dilator 24 is stored with a device extending through the inner cavity 74, the device may directly engage and/or contact the raised portion and not primarily with the sealing surface 309. As such, the raised portion can prevent damage to the sealing surface 309 of the sealing element 308 caused by extended forceful contact with the device during storage and, thus, can extend the sealing capability and life of the valve element 300.

Sealing portion 308 of the valve element 300 can comprise any of a variety of materials that can substantially seal inner cavity 74 when in contact with or biased against sealing surface 75. In some embodiments, sealing portion 308 can comprise metal, plastic, rubber, or other suitable biocompatible materials such as polyisoprene, silicone, polyurethane, or other elastic polymers. In some embodiments, the sealing portion 308 can be coated or include other surface treatments, such as a siliconized surface to facilitate low-friction sliding of various elements along its surface (such as guidewire 28). The attachment portion 304 and the sealing portion 308, in some instances, can be formed of the same material, such that the valve element 300 can optionally be a single unitary piece. In some embodiments, the valve element 300 can comprise a separate biasing element configured to bias the valve element 300 towards the closed position.

The valve element 300 can be formed in a number of different ways, such as by molding (e.g., injection), stamping and the like, and can be formed separately or integrally with the dilator hub 38. The attachment portion 304 and the sealing portion 308 can be attached to each other and/or the dilator hub 38 in a variety of ways, such as with adhesive, bonding (e.g., ultrasonic, thermal, etc.), fasteners, overmolding, and the like. A primer or non-stick coating or surface treatment can be applied to the attachment portion 304 and/or the sealing portion 308 to facilitate their attachment to each other during the manufacturing thereof. With respect to the bending properties of the sealing portion 308, described above, in some embodiments the sealing portion 308 can be pretreated to have certain mechanical characteristics prior to its combination with the attachment portion 304.

The valve element 300, as depicted by way of the attachment portion 304, can attach to the dilator hub 38 by a variety of means. In some embodiments, it can be glued or bonded to the dilator hub 38. In other embodiments, the attachment portion 304 can attach to the dilator hub 38 by molding or overmoulding. In further embodiments, the attachment portion 304 can be molded integrally with the dilator hub 38 (or a portion thereof). When formed integrally, it may be desirable to give the dilator hub 38 a substantially greater thickness than the attachment portion 304, such that the dilator hub 38 maintains a higher rigidity. In other embodiments, the attachment portion 304 can attach to the dilator hub 38 by a mechanical compression, such as where the dilator hub 38 includes a groove that receives the attachment portion 304, and allows it to be press-fit into position.

Figure 7:
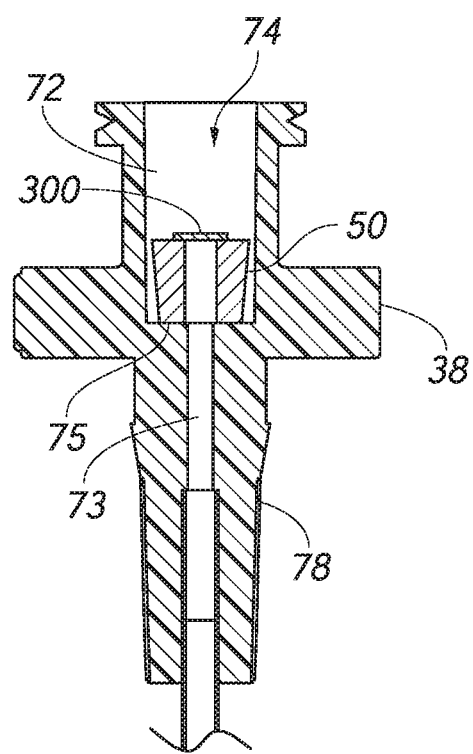
FIG. 7 is an enlarged side cross-sectional view of an embodiment of a dilator hub including an attachment member engaged with a valve element.

In some embodiments, the valve element 300 may engage the dilator hub 38 through an attachment member 50, as shown in FIG. 7. The valve element 300 may be attached to an attachment member 50, which is inserted into the inner cavity 74 of the dilator hub 38. The attachment member 50 can include a central bore configured to engage the sealing portion 308 of the valve element 300 when the valve element 300 is in a closed position. A distally-facing surface of the attachment member 50 can be substantially straight or flat to engage the sealing surface 75 of the dilator hub 38. The attachment member 50 is placed against the sealing surface 75 so that in a closed position, the sealing portion 308 seals against the attachment member 50 rather than the sealing surface 75. The attachment member 50 can be made of a relatively soft material and can be soft enough to allow the attachment member 50 to be press-fit into the inner cavity 74.

The attachment member 50 can be substantially circular, or donut-shaped, allowing flexibility in its rotational position within the dilator hub 38. However, in other embodiments the attachment member 50 can be rotationally fixed within the dilator hub 38, i.e., with a non-circular insert and a corresponding non-circular receiving portion in the dilator hub 38. Further, the outer edge of the attachment member 50 can be shaped to substantially match the sealing surface 75 of the dilator hub 38 to form a seal between the two that at least hinders the escape of fluids therethrough. In some embodiments, a taper along the attachment member 50 and/or within the dilator hub 38 can facilitate a seal between the attachment member 50 and the dilator hub 38.

The attachment member 50 can advantageously compensate for possible molding imperfections and/or misalignment in the manufacture and assembly of the dilator hub 38, for example, due to being constructed from a relatively soft and compliant material. The attachment member 50 may also advantageously reduce the size of the aperture to be sealed by the sealing portion 308 compared to the sealing surface 75. Additionally, the attachment member 50 can act as a seal around a device inserted through the dilator hub 38 to maintain a seal when the valve element 300 is in an open position to accommodate the device. The attachment member 50 can therefore act as a seal independent of the sealing portion 308. In some embodiments, the attachment member 50 can stretch to accommodate and/or conform to various devices that can be introduced through the dilator hub 38.

In some embodiments, the sealing portion 308 can be made of a relatively hard material, for example, polyurethane or polycarbonate. Inclusion of a relatively soft attachment member 50 can advantageously allow the sealing portion 308 to be made of a relatively hard material because the more compliant attachment member 50 can compensate for molding imperfections, misalignment, and the like for which a relatively hard sealing portion 308 may not be able to compensate as effectively. The relatively hard material can advantageously reduce possible damage to the valve element 300 and better resist tearing and/or other wear. Such tearing or wear can adversely affect the effectiveness of the seal.

The attachment member 50, in some instances, can be removably engaged with at least a portion of the dilator hub 38 so that the attachment member 50 can move in or out of the inner cavity 74. For example, the attachment member 50 may be removably held within the inner cavity 74 via any suitable interaction (e.g., interference, engagement, friction, mechanical coupling, adhesion, etc.). The attachment member 50 may be sufficiently engaged with the dilator hub 38 to prevent unintentional removal of the attachment member 50 from the inner cavity 74. In some embodiments, once the guidewire 28 abuts against the valve element 300, further proximal movement of the guidewire 28 relative to the dilator 24 may be insufficient to overcome the interactive force removably holding the attachment member 50 within the inner cavity 74. For example, the attachment member 50 may remain within the inner cavity 74 after the guidewire 28 presses against and extends past the valve element 300. In certain embodiments, one or more walls such as sealing surface 75 of the inner cavity 74 prevent distal movement of the attachment member 50 relative to the inner cavity 74.

The dilator hub 38 may include locking structures along a proximal region and/or a distal region 70 of the dilator hub 38. Each locking structure may be a luer type or other type of connection. In the illustrated embodiment, the dilator hub 38 comprises a luer connection 78. In some embodiments, the luer connection 78 (e.g., a male luer slip connector) can be configured to engage to the sheath hub 42 (e.g., a female luer slip connector) on the sheath 26 illustrated in FIGS. 8A and 8B. Additionally, the male-female lure slip connectors on these components can be reversed.

The color of the dilator 24 may be selected to enhance the contrast between the blood or other fluid and the dilator 24. For example, in some applications, during blood flash, blood is observed flowing between the dilator 24 and the sheath 26 to confirm proper placement in a blood vessel. To increase the visibility of the fluid as the fluid flows between the sheath 26 and dilator 24, the sheath 26 is preferably manufactured from a clear or transparent material with the dilator 24 having a color that contrasts with the color of the fluid. For example, the dilator 24 may have a white color to enhance its contrast with red blood. Other colors of dilator 24 could be employed depending on the color of the fluid and the degree of contrast desired. Further, only a portion of the dilator 24 in the region of the blood flash can have the contrasting color with the remainder having a different color.

In use, the dilator 24 expands an opening or passage created by the needle 22. The expanded passage facilitates subsequent introduction of the sheath 26. The needle 22 allows the introduction of the guidewire 28, and subsequently the dilator 24 and finally the sheath 26 into a patient's body.

Figure 8A:
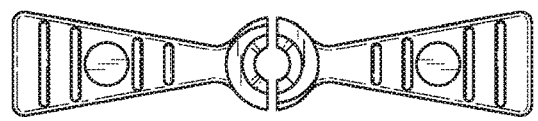
FIG. 8A is an end view of a sheath looking in a distal direction.
Figure 8B:
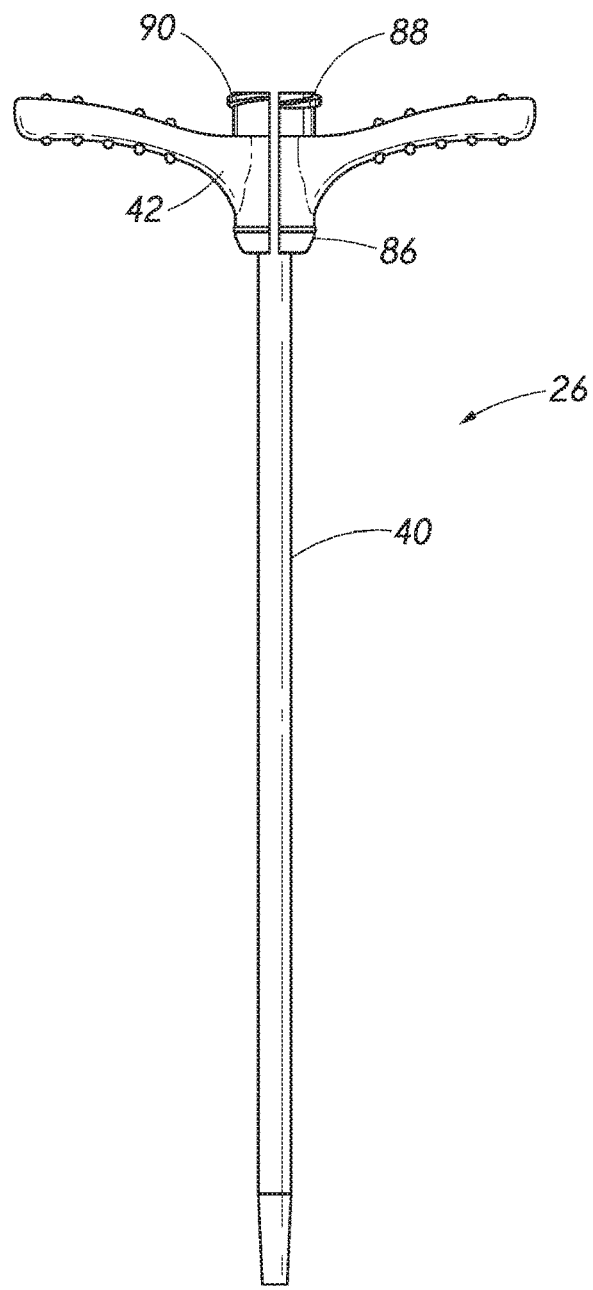
FIG. 8B is a side view of the sheath of FIG. 8A.

FIG. 8A is an end view of a sheath 26 looking in the distal direction that can be used with the access device 20 of FIG. 1. FIG. 8B is a side view of the sheath 26 depicted in FIG. 8A. The sheath 26 may comprise a sheath body 40, a sheath hub 42, a distal region 86, and a proximal region 88. The sheath body 40 may be made partially or completely from clear, translucent, transparent, or semi-opaque material. The sheath body 40 can also include one or more radiopaque markers, such as, for example, barium sulfate stripes. In a preferred embodiment, the sheath includes two such radiopaque stripes disposed on diametrically opposite sides of the body 40.

The sheath body 40 may be a single piece sheath through which a catheter or other medical article (e.g., guidewire 28) is inserted through the sheath 26. In such an embodiment, the sheath body 40 forms a conduit for insertion of the catheter or other medical article. In addition to providing a conduit, the sheath 26 or a portion of the sheath can form a lumen that is in addition to the lumen(s) of the catheter. For example, an equivalent to a triple lumen catheter can be formed by inserting a dual lumen catheter through the sheath body 40 with the sheath body 40 itself forming a third lumen. The sheath body 40 can be manufactured from a clear or at least somewhat transparent material to allow the physician or healthcare provider to see blood flowing within the dilator 24 through the sheath body 40.

In some embodiments, for example as shown in FIGS. 8A and 8B, the sheath can be a splittable sheath 26A. For example, it may be advantageous to remove a portion or the entire sheath body 40 depending on the type of catheter or medical article that is to be inserted into the vessel after employing the access device 20. For example, after the catheter or other medical article is inserted into the vessel, a portion of the sheath body 40 can be separated or peeled-away and removed to reduce clutter at the access site. A peel-away sheath can include perforations, serrations, skives, or other structures, or include other materials (e.g., PTFE with bismuth) to allow the physician or healthcare provider to remove easily a portion or the entire sheath body 40.

The sheath hub 42 may include a luer slip connection 90. The luer slip connection 90 may comprise a locking or attaching structure that mates or engages with a corresponding structure. For example, the luer slip connection 90 can be configured to engage with the luer connection 78 of the dilator hub 38.

The sheath hub 42, as best seen in FIG. 8A, preferably is designed so that the luer connection 78 of the dilator hub 38 can enter the sheath hub 42 substantially unobstructed. However, in use, once the sheath hub 42 is placed at a desired location over the dilator shaft 36, the physician or healthcare provider can push, pull, or twist the sheath hub 42 and possibly disengage or engage the luer slip connection 90 with a corresponding connector on another medical article. The luer slip connection 90 creates a mechanical fit so that the dilator hub 38 and the sheath hub 42 are releasably interlocked. The sheath hub 42 engages with the corresponding luer connection 78 on the dilator hub 38. The locked position can be disengaged or engaged by pulling, squeezing, pushing or twisting the dilator hub 38 relative to the sheath hub 42.

In additional embodiments, the sheath hub 42 may comprise radially extending wings or handle structures to allow for easy release and removal of the sheath body 40 from other parts of the access device 20. In some applications, the wings are sized to provide the healthcare provider with leverage for breaking apart the sheath hub 42. The sheath hub 42 and/or the sheath body 40 may comprise two or more portions (e.g., halves) connected by a thin membrane. The membrane can be sized to hold the two or more portions of the sheath hub 42 and/or sheath body 40 together until the healthcare provider decides to remove the sheath hub 42 and/or sheath body 40 from the access device. The healthcare provider manipulates the wings to break the membrane and separate the sheath hub 42 into removable halves.

Figure 9:
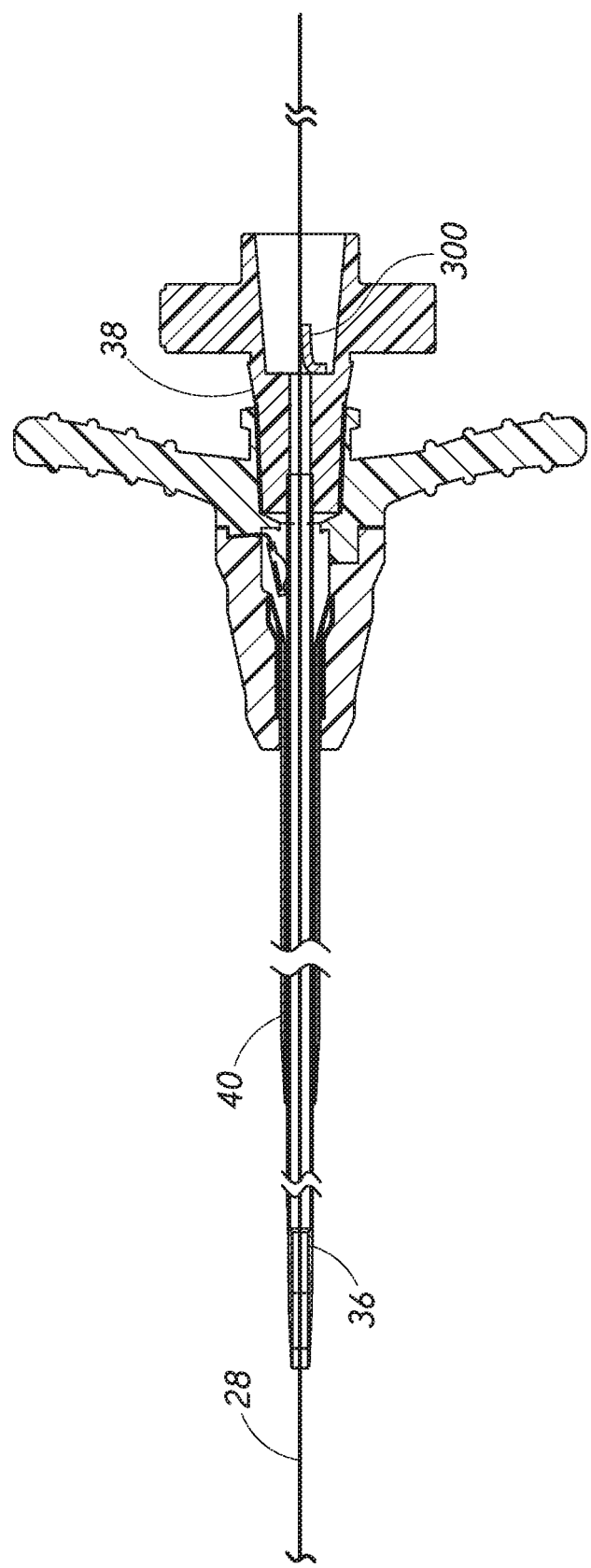
FIG. 9 is a cross-sectional view of an access device including the dilator of FIG. 3A coaxially disposed about the sheath of FIG. 8A after the access device has been threaded over a guidewire.

FIG. 9 is a side cross-sectional view of the access device 20 after the access device 20 has been threaded over the guidewire 28. Thus, in the illustrated embodiment, the dilator 24 includes the dilator shaft 36 that extends distally from the dilator hub 38, and the sheath 26 includes the sheath body 40 that extends distally from the sheath hub 42. In certain embodiments, the guidewire 28 includes a guidewire hub or cap (not shown). In the illustrated embodiment, the dilator 24 and the sheath 26 are releasably interlocked at a proximal end of the access device 20. In some embodiments, the releasable interlock between the dilator 24 and the sheath 26 is a linear interlock where the sheath 26 is locked to the dilator 24. The relative positioning of the terminal ends of the dilator 24 and the sheath 26 are shown in FIG. 9. For example, the terminal end of the dilator body 36 extends beyond the terminal end of the sheath 26.

Figure 10B:
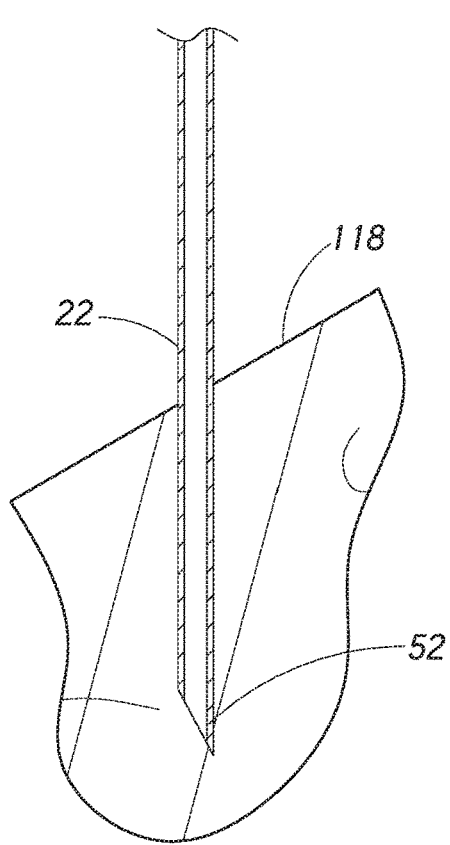
FIG. 10B is an enlarged side cross-sectional view of a distal end of the needle of FIG. 10A which is circled by line 10B-10B.
Figure 10A:
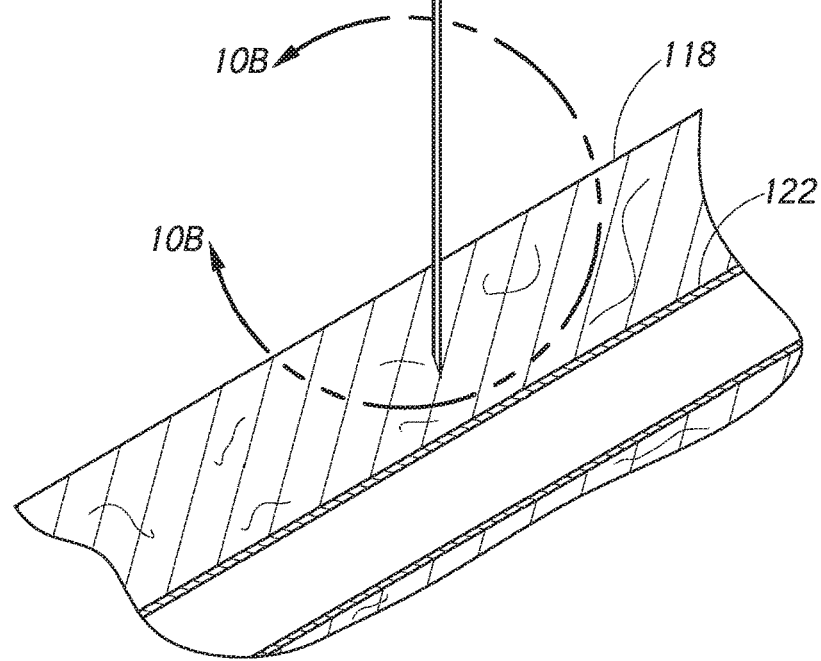
FIG. 10A is a side cross-sectional view of the needle of FIG. 2A penetrating a body.
Figure 11B:
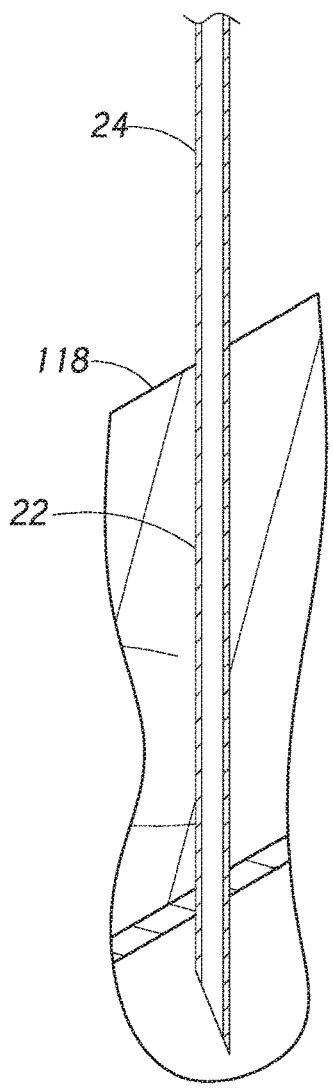
FIG. 11B is an enlarged side cross-sectional view of a distal end of the needle of FIG. 11A which is circled by line 11B-11B.
Figure 11A:
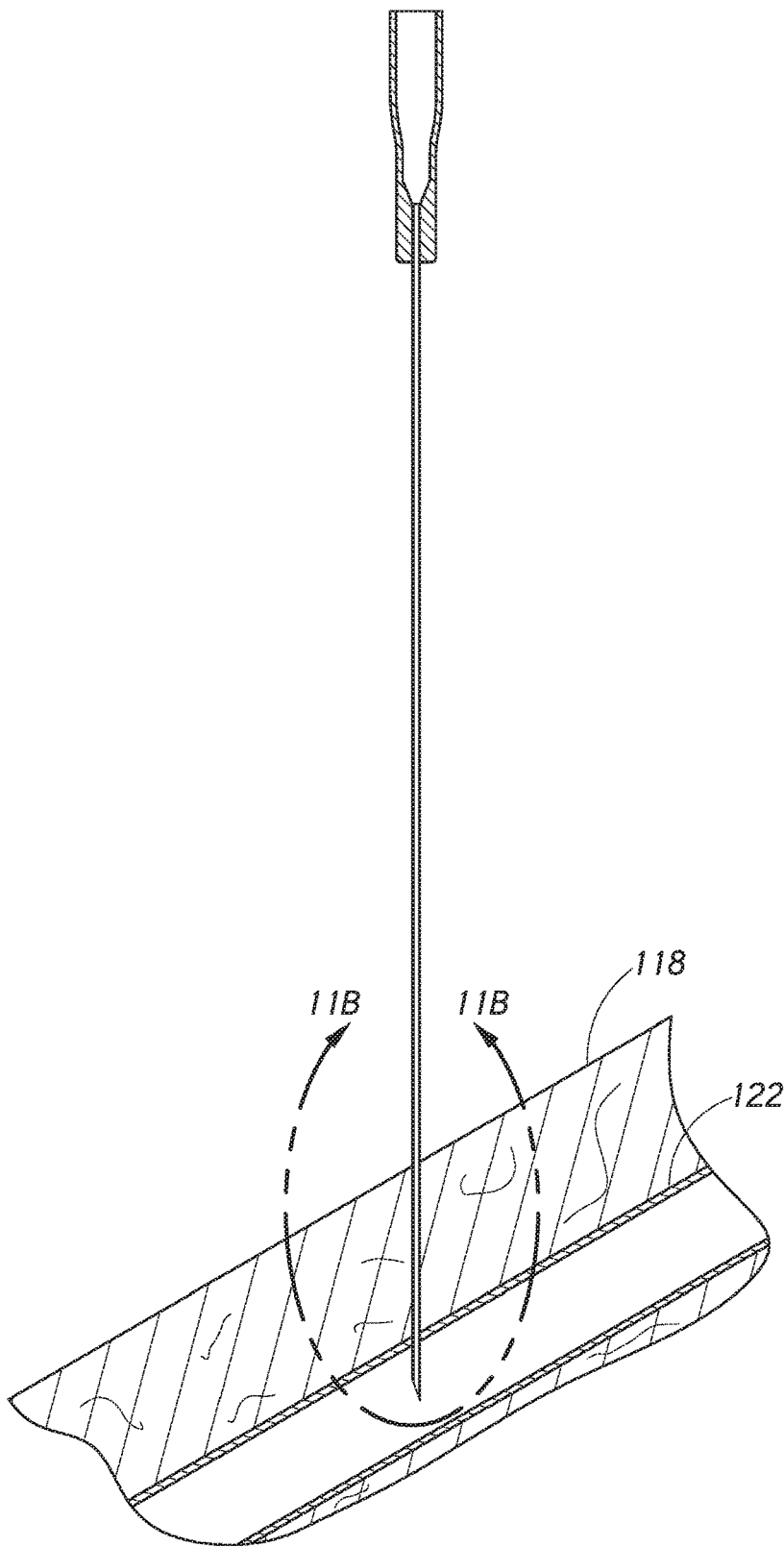
FIG. 11A is a side cross-sectional view of the needle of FIG. 10A where the needle has penetrated a vasculature.

FIG. 10A is a cross-sectional view of the needle 22 illustrated in FIG. 2A penetrating a body 118. FIG. 10B is an enlarged partial cross-sectional view from FIG. 10A of a distal end of the needle 22. In FIG. 11A, the needle 22 has penetrated the vasculature. FIG. 11B is an enlarged partial cross-sectional view from FIG. 11A of a distal end of the needle 22. In use, the bevel tip 52 enters the blood vessel 122.

Figure 12:
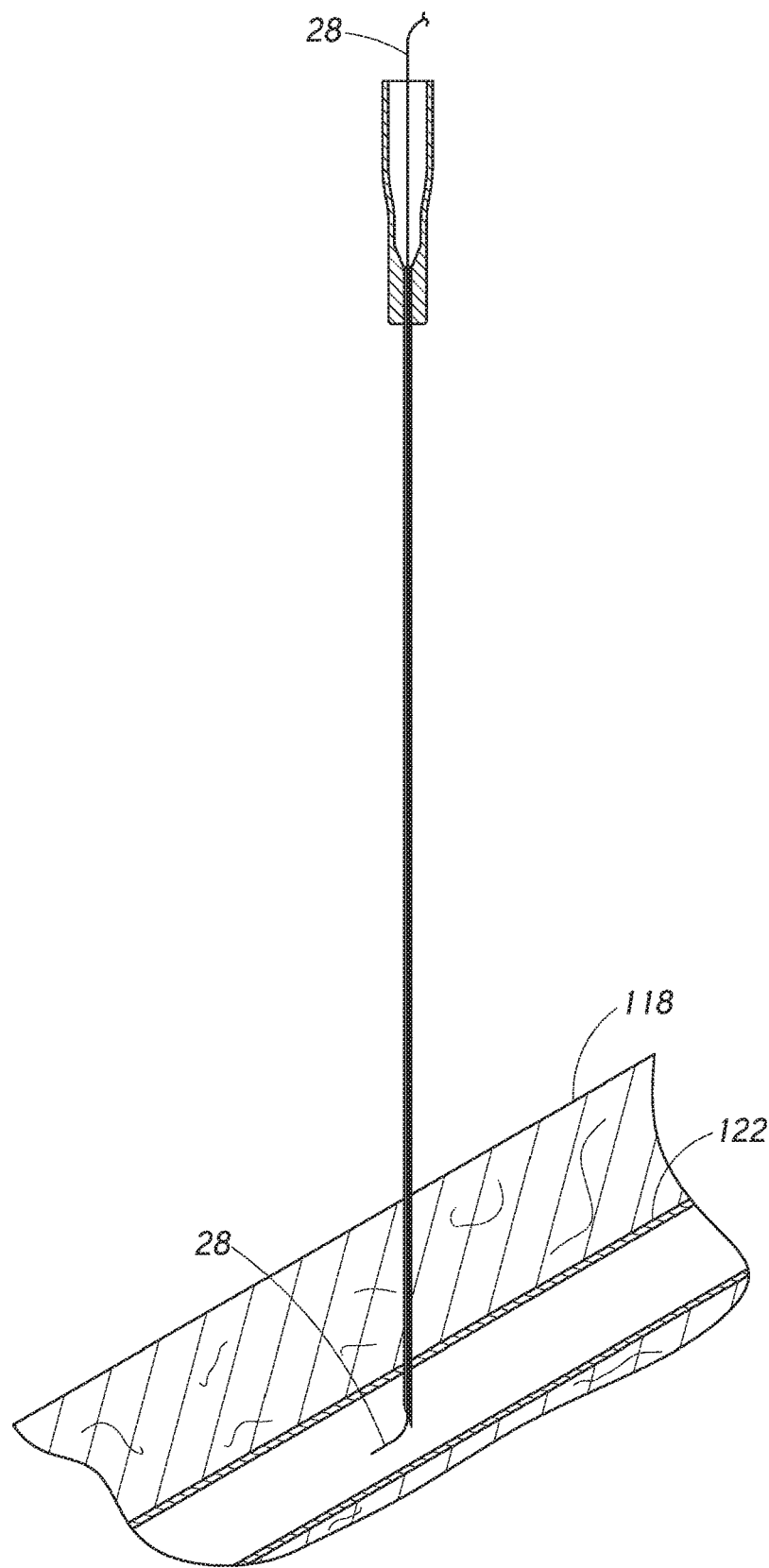
FIG. 12 is a side cross-sectional view of the needle of FIG. 11A where a guidewire has been fed through the needle and into the vasculature of the patient.

FIG. 12 is a cross-sectional view similar to FIG. 10A where a guide wire 28 has been fed through the needle 22 and into the blood vessel 122 of the patient. Once the physician or healthcare provider has located the needle 22 within the target blood vessel 122, the physician or healthcare provider feeds the guidewire 28 into the vasculature. The needle 22 is held still while the guidewire 28 is fed through the needle 22 and into the patient. During the insertion procedure, the guidewire 28 passes through the interior bore 54 of the needle 22.

Figure 13:
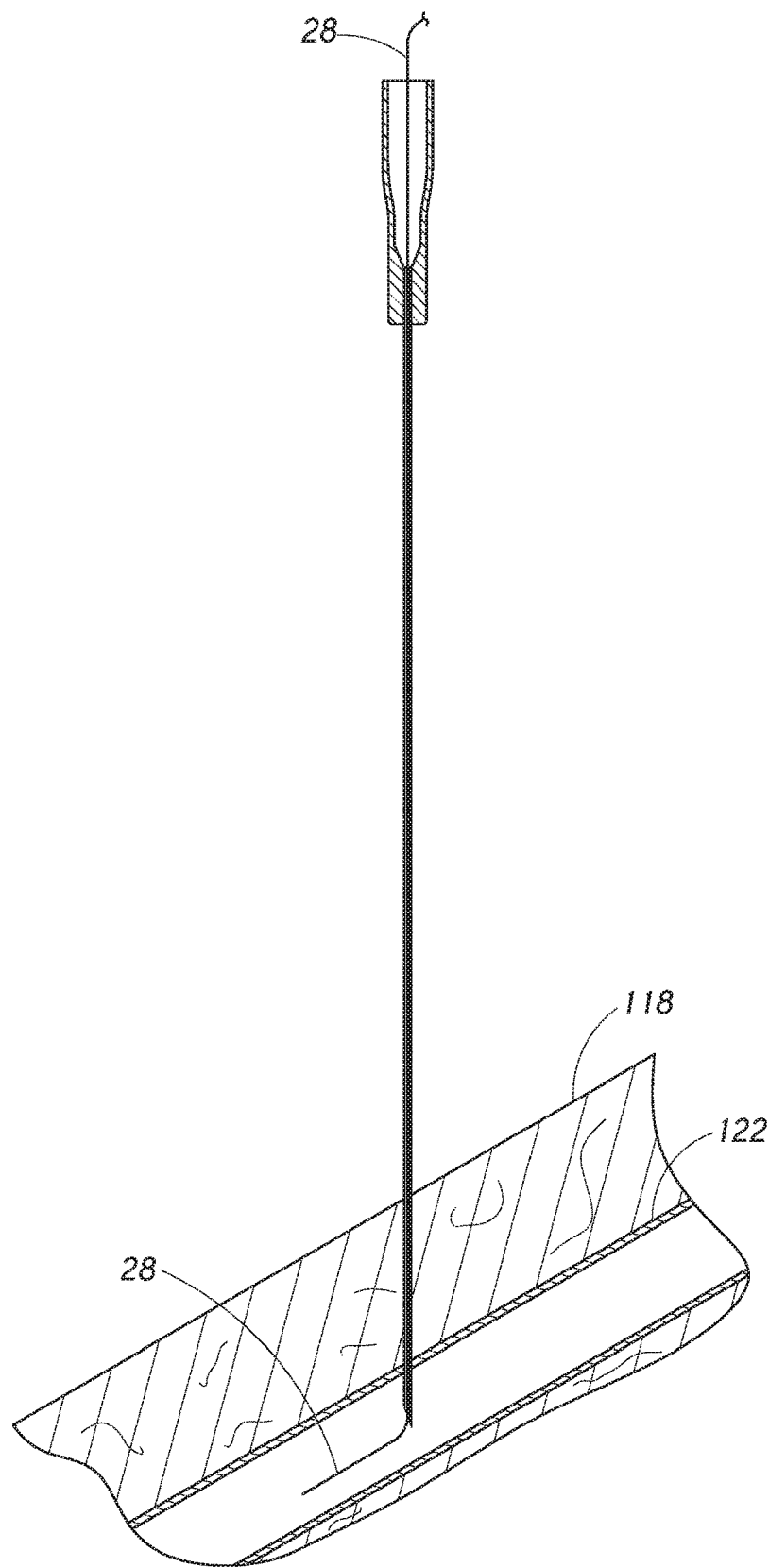
FIG. 13 is a side cross-sectional view of the needle of FIG. 12 where the guidewire has been extended into the vasculature of the patient for the needle.

A guide wire advancer as known in the art may be employed when feeding the guidewire 28 through the needle 22. For example, if the guidewire 28 has a curved or J tip, an advancer may be employed to straighten the tip facilitating feeding of the guidewire 28 into the interior bore 54 of the needle 22. FIG. 13 is a cross-sectional view similar to FIG. 12 except the guidewire 28 has been extended further into the vasculature of the patient.

Figure 14A:
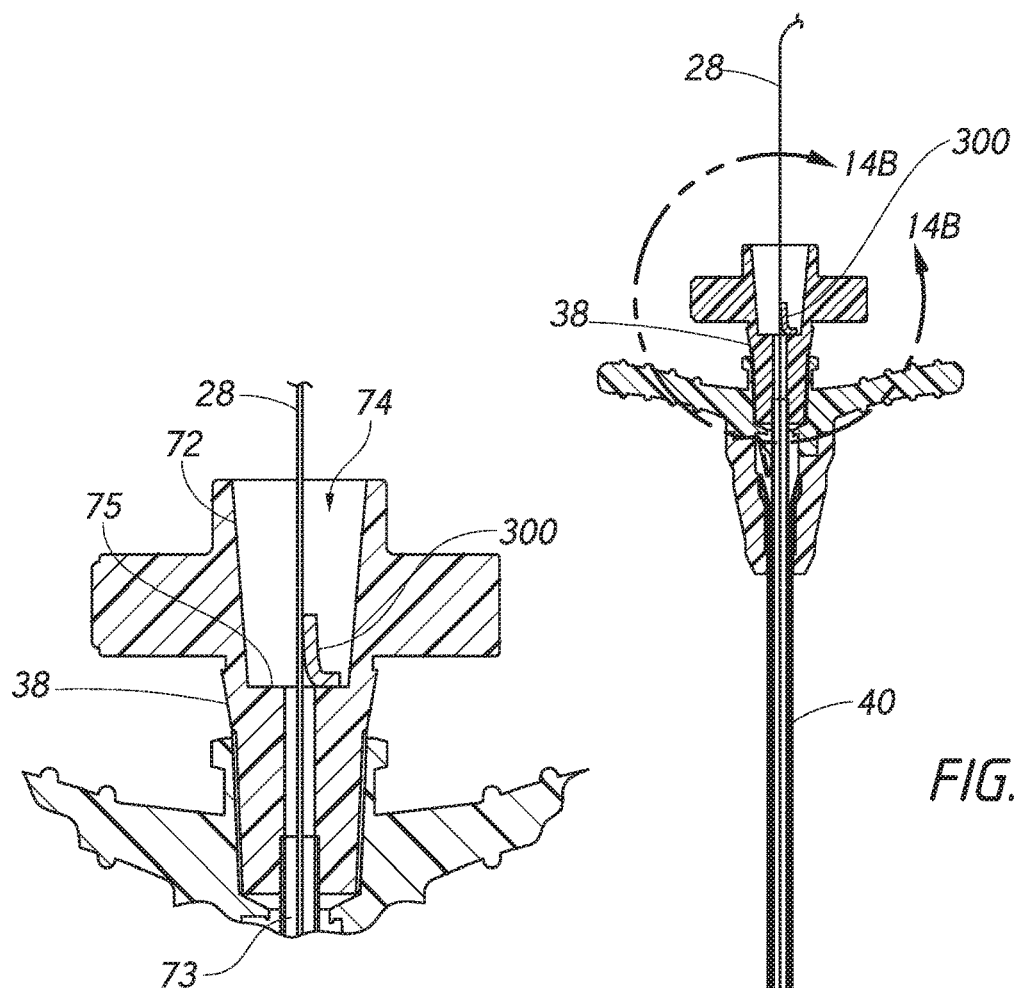
FIG. 14A is a side cross-sectional view of the access device of FIG. 9 that has been slid along the exterior portion of the guidewire of FIG. 13, with the needle having been already withdrawn and slid off the guidewire until the guidewire passes through the dilator.
Figure 14B:
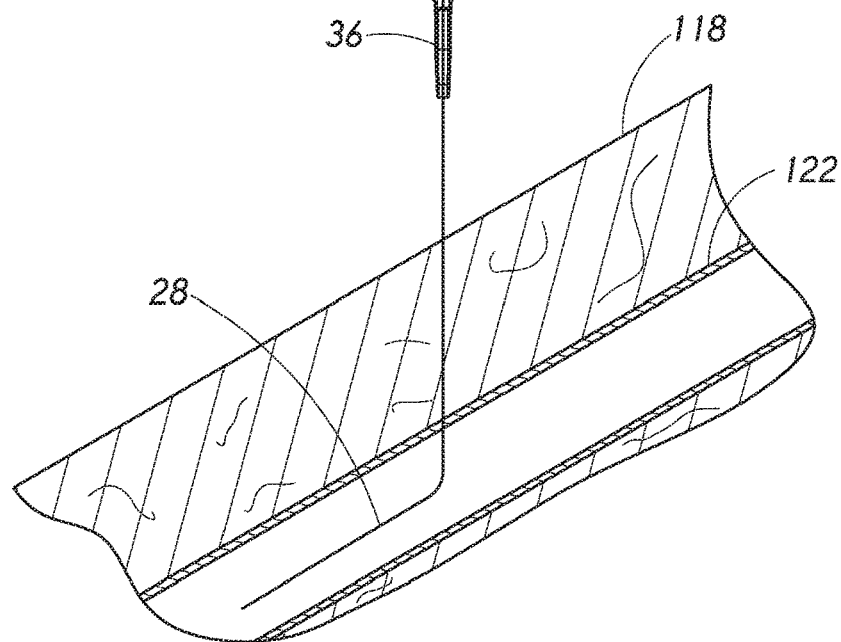
FIG. 14B is an enlarged side cross-sectional view of a portion of the access device of FIG. 14A which is circled by line 14B-14B.

FIG. 14A is a cross-sectional view similar to FIG. 13 where the needle 22 has been removed and the dilator 24 and the sheath 26 have been slid along the exterior portion of the guidewire 28 causing the valve element 300 to be moved into the open position. FIG. 14B is an enlarged partial cross-sectional view from FIG. 14A. The sealing portion 308 of the valve element 300 within the inner cavity 74 of the dilator 24 has effectively been moved in a proximal direction relative to the dilator 24 as the dilator 24 is slid along the exterior portion of the guidewire 28.

Figure 15:
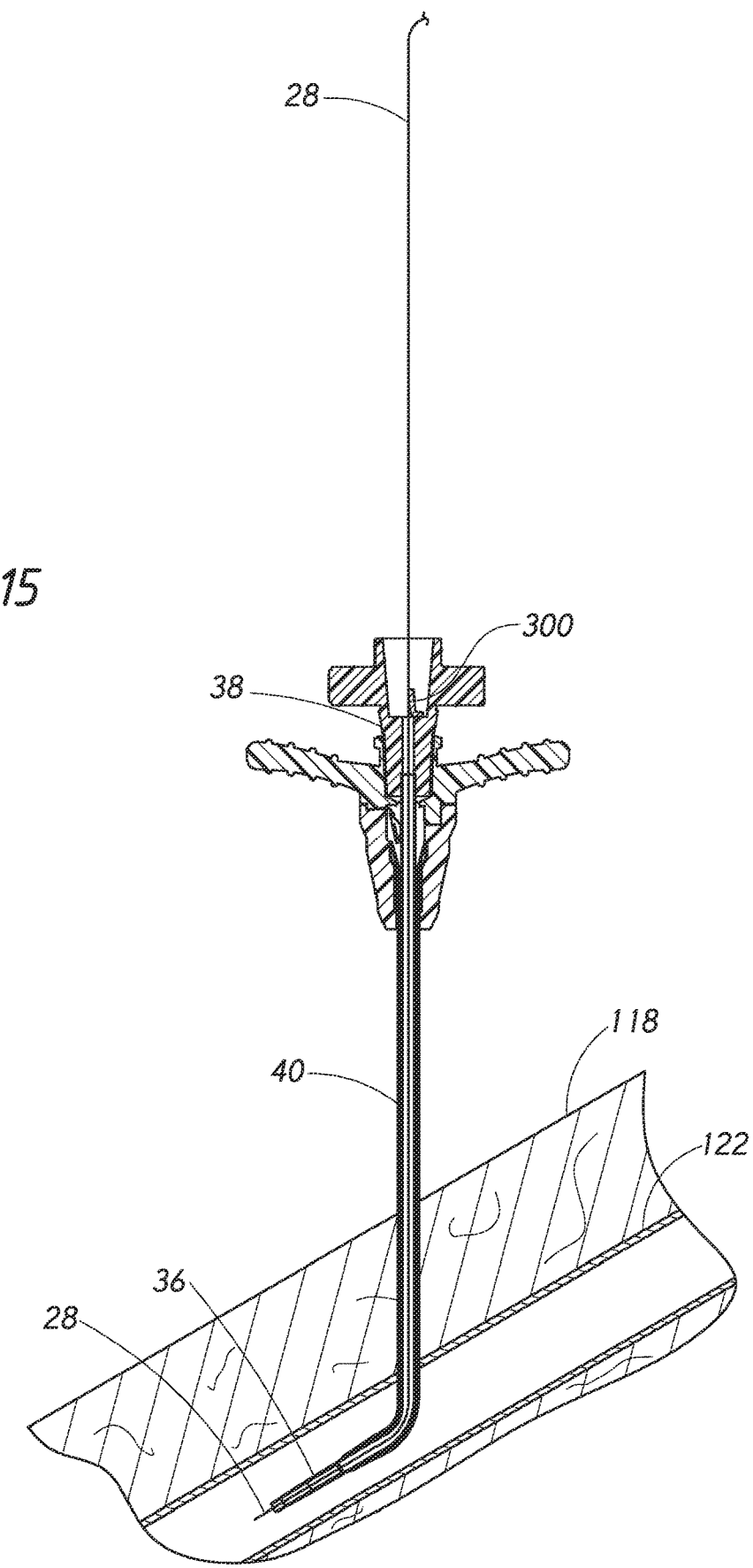
FIG. 15 is a side cross-sectional view of the access device of FIG. 14A where the access device has been slid further along the exterior portion of the guidewire and into the patient's vasculature.

FIG. 15 is a cross-sectional view similar to FIG. 14A where the dilator 24 and sheath 26 have been slid further along the exterior portion of the guidewire 28 and into the patient's vasculature. During threading of the sheath 26 and the dilator 24 over the guidewire 28 and into the blood vessel 122, the guidewire 28 can freely slide along the valve element 300. The dilator 24 and sheath 26 may be inserted into the patient's vasculature at any one of a variety of angles relative to the body 118 of the patient. The angle of insertion shown in FIG. 15 is for schematic illustrative purposes only. In some embodiments, the dilator 24 and the sheath 26 may be introduced at a lower profile angle relative to the body 118 when compared to the angle of insertion shown in FIGS. 15-20. In this arrangement, the dilator 24 and the sheath 26 can be inserted such that a distal end portion of the dilator 24 and/or the sheath 26 need not bend (or bend only slightly) once inserted into the blood vessel 122 (e.g., as compared to the dilator 24 and sheath 26 shown in FIGS. 15-20).

Figure 16:
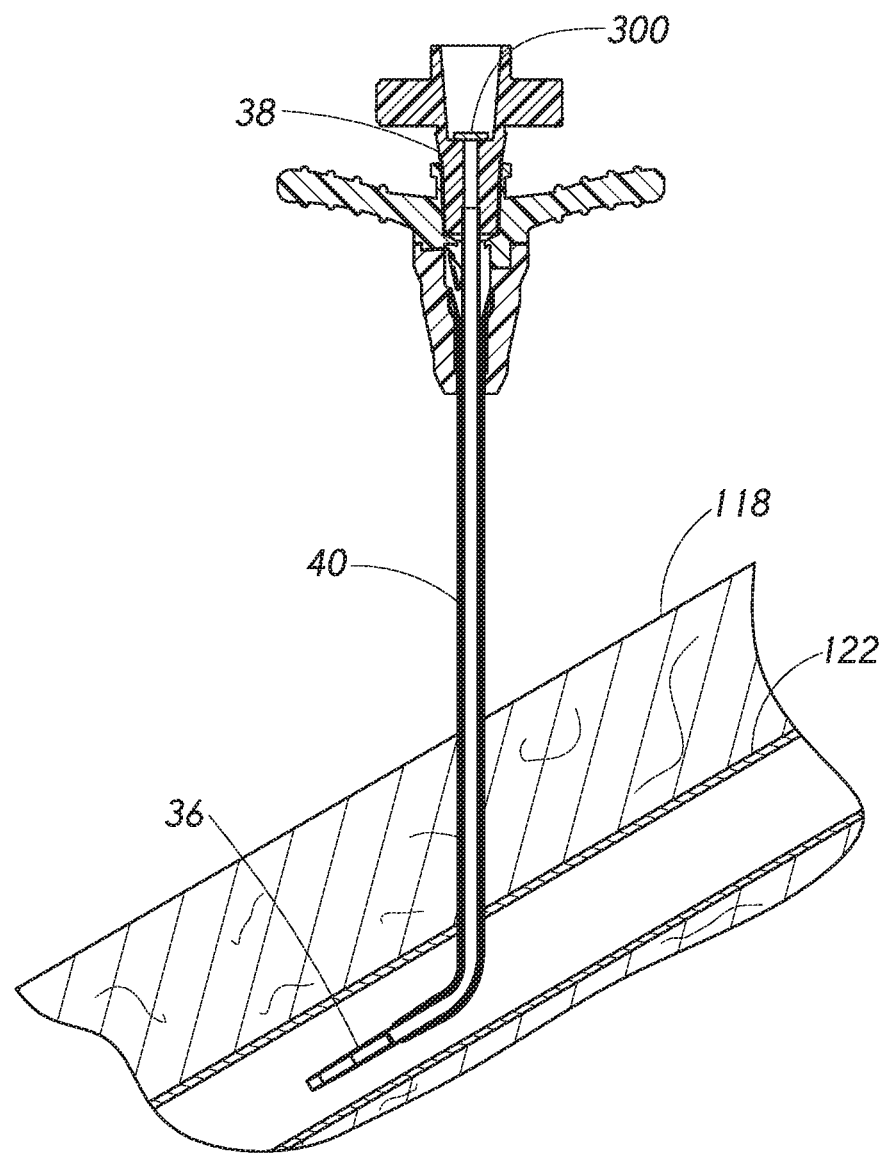
FIG. 16 is a side cross-sectional view of the access device of FIG. 15 where the guidewire have been withdrawn from the access device causing the valve element of the dilator to be moved into the closed position.

FIG. 16 is a cross-sectional view similar to FIG. 15 where the guidewire 28 has been withdrawn from the dilator 24 and the sheath 26. As described herein, the valve element 300 can be biased towards the center of the dilator hub 38. The bias can cause the valve element 300 to move towards the closed position when the guidewire 28 is removed. Accordingly, upon removal of the guidewire 28, the valve element 300 may move to the closed position to substantially seal at least the distal portion 73 of the inner cavity 74 by abutting against the sealing surface 75, as shown in FIG. 16.

Figure 17:
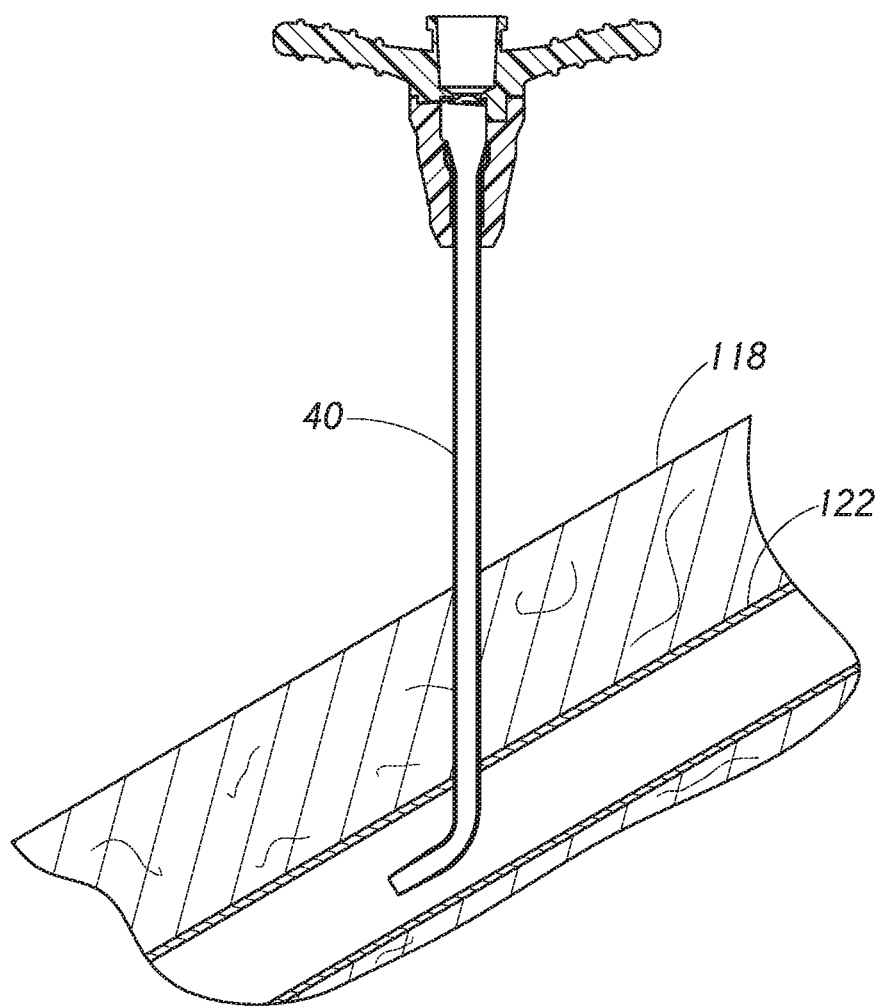
FIG. 17 is a side cross-sectional view of the access device of FIG. 18 where the dilator has been withdrawn from the vasculature and the sheath.

FIG. 17 is a cross-sectional view similar to FIG. 16 where the dilator 24 has been removed from the patient and the sheath 26. The sheath 26 is left properly inserted within the blood vessel 122. The dilator 24 may be removed after or in concert with removal of the guidewire 28.

Figure 18:
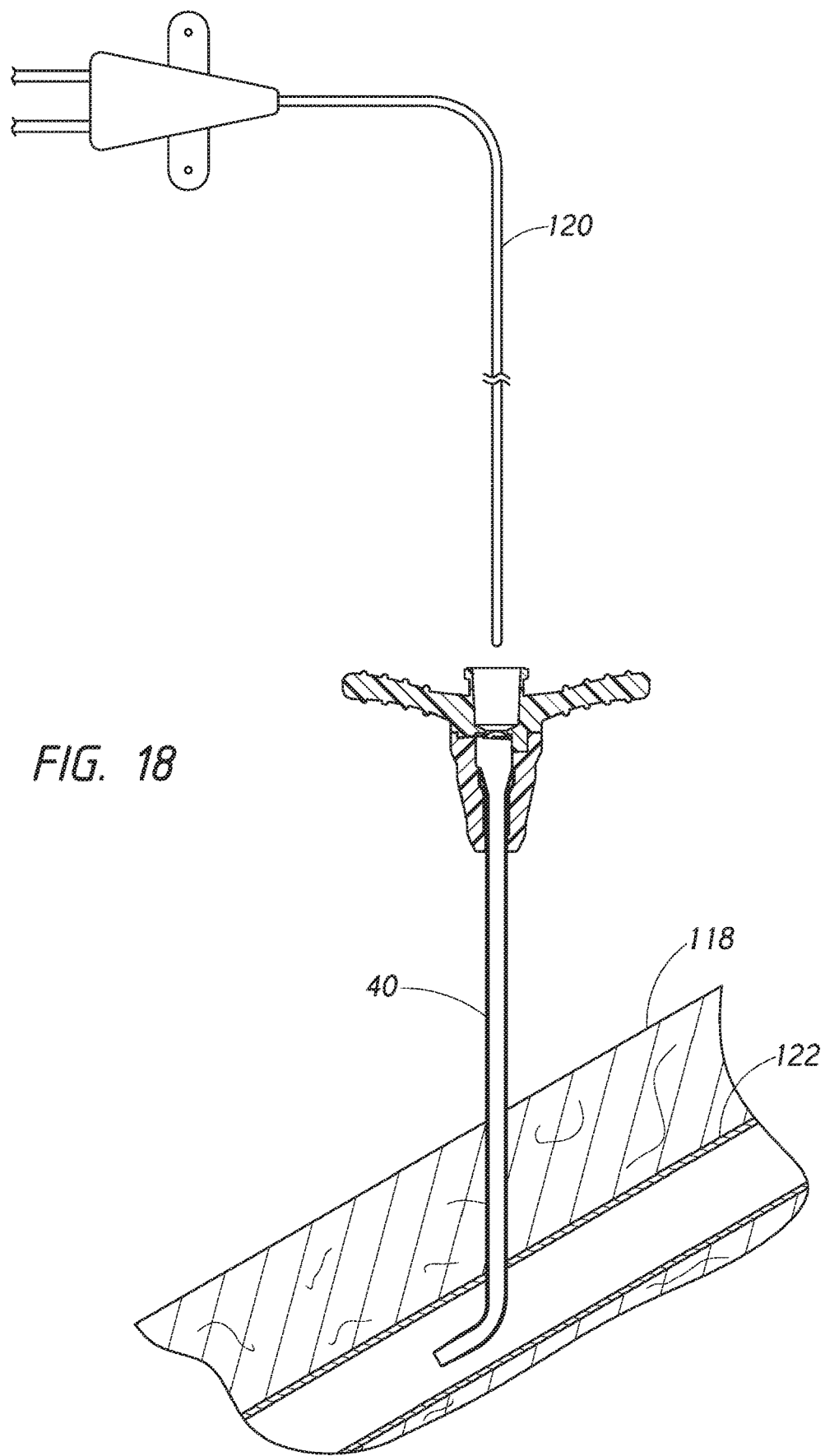
FIG. 18 is a side cross-sectional view of the sheath of FIG. 17 where a catheter is aligned with the sheath for insertion into the patient's vasculature.
Figure 19:
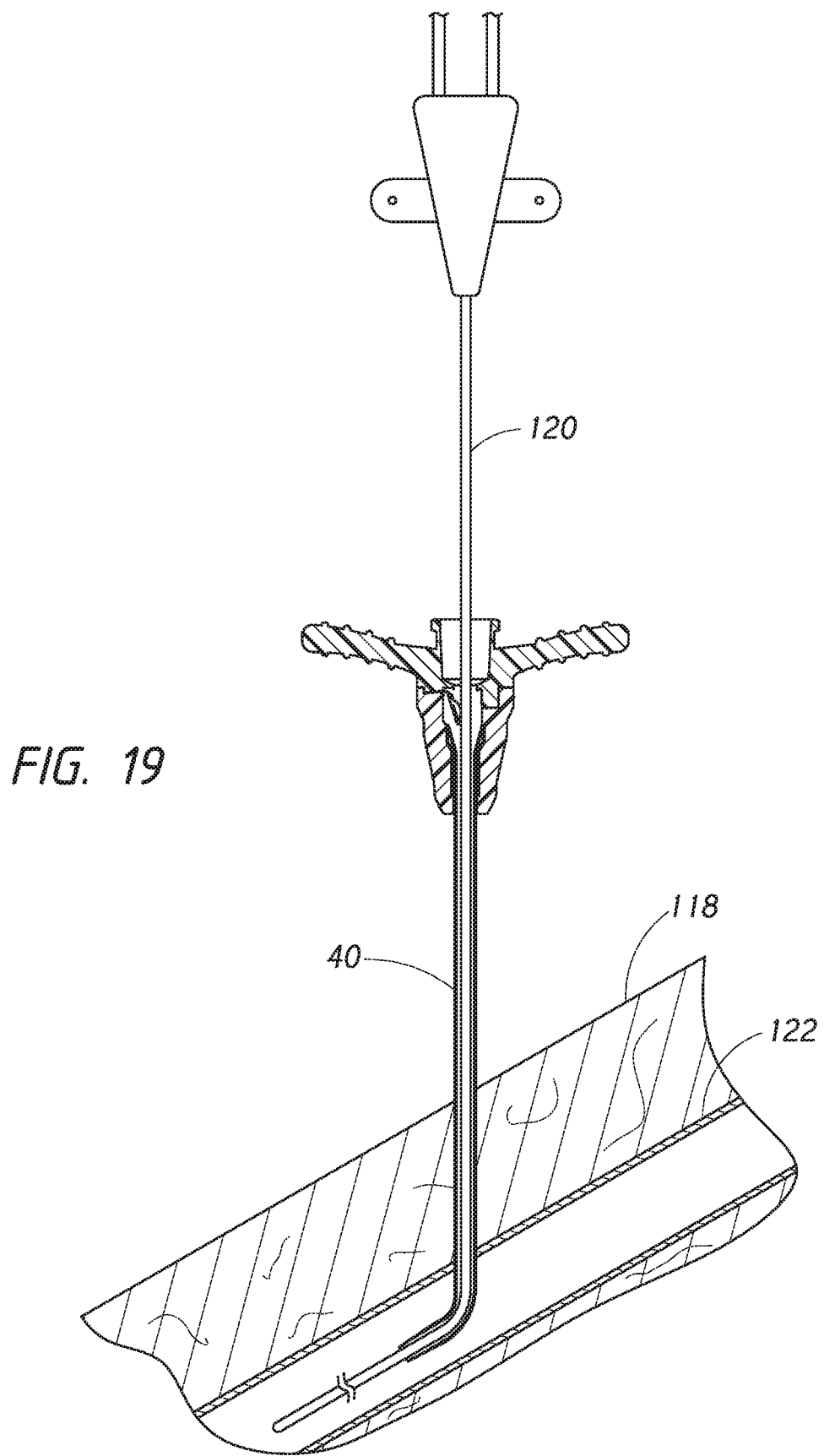
FIG. 19 is a side cross-sectional view of the sheath of FIG. 18 where the catheter has been inserted through the sheath and into the patient's vasculature.

FIG. 18 is a cross-sectional view similar to FIG. 17 where a catheter 120 is aligned with the sheath 26 for insertion into the patient's vasculature. FIG. 19 is a cross-sectional view similar to FIG. 18 where the catheter 120 has been inserted through the sheath 26 and into the patient's vasculature, specifically the targeted blood vessel 122.

Figure 20:
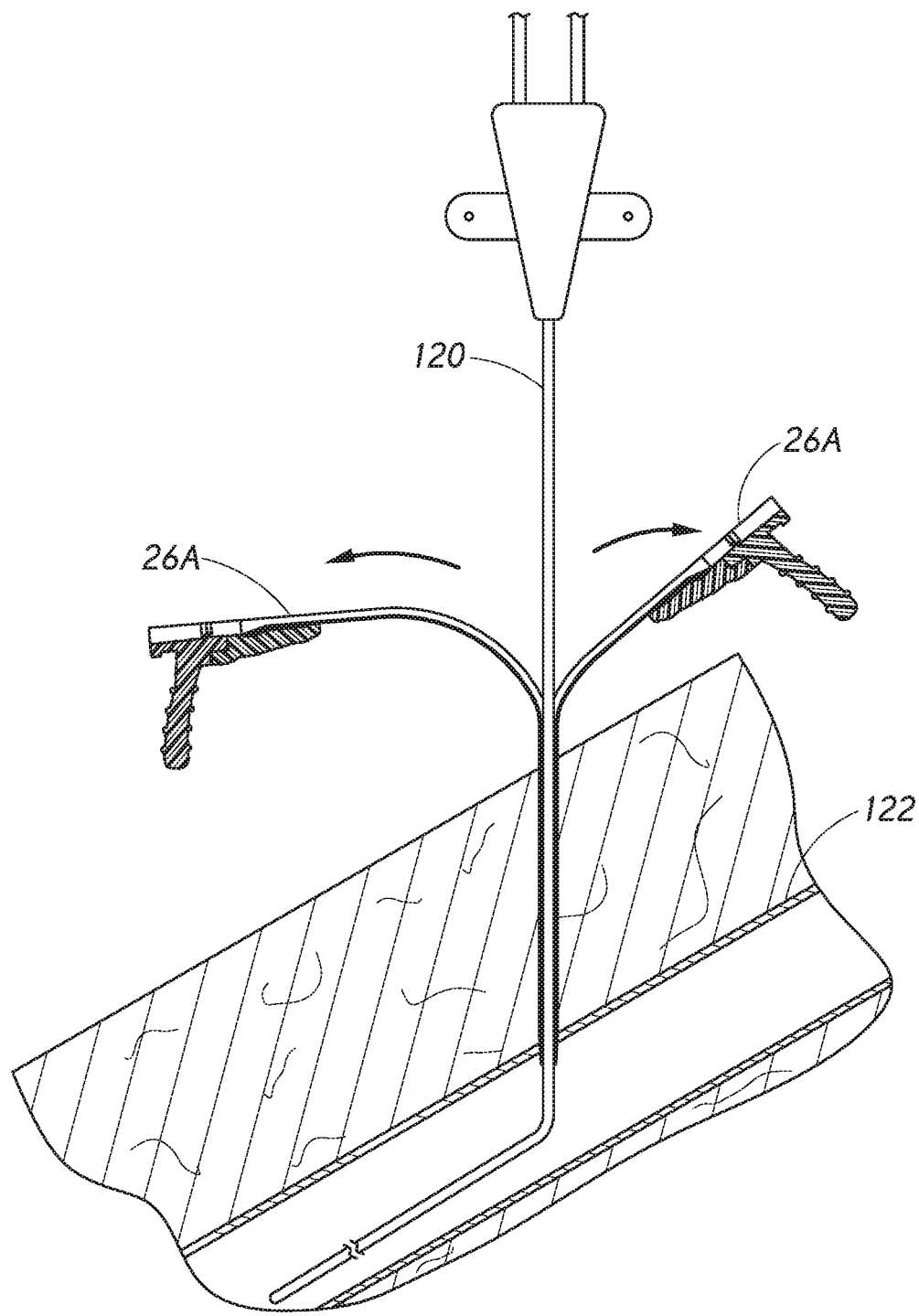
FIG. 20 is a side cross-sectional view of the sheath of FIG. 19 where two portions of the sheath are being peeled away from each other to remove the sheath from encircling the catheter.

FIG. 20 is a cross-sectional view similar to FIG. 19 where two portions of the sheath 26 are being peeled away from each other to remove the sheath 26 from encircling the catheter 120. The sheath 26 is splittable along one or more split lines. A splittable sheath 26 provides the advantage of allowing a portion of or the entire sheath body 40 to be removed depending on the type of catheter or medical article that is to be inserted into the vessel after employing the access device 20. For example, after the catheter 120 is inserted into the blood vessel 122, a portion of the sheath body 40 is separated or peeled-away and removed to reduce clutter at the access site. The peel-away sheath 26 can be first slid in a proximal direction along the catheter 120 until the sheath 26 is removed from the patient and then split apart. Alternatively, the sheath 26 can be initially split prior to the entire sheath 26 being removed from the patient. After the remainder of the sheath 26 is removed from the patient, the physician or healthcare provided can continue splitting the sheath 26. The sheath 26 could be split in concert with its removal from the patient as is illustrated in FIG. 20. In certain embodiments, the sheath 26 is not splittable.

As noted above, the present access device can be used to place a catheter at other locations within a patient's body. Thus, for example, but without limitation, the access device can be used as or with a variety of catheters to drain fluids from abscesses, to drain air from a pneumotorax, and to access the peritoneal cavity.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. An access device for placing a medical article within a body space, the access device comprising:
   a dilator comprising:
      an elongated dilator body, and
      a dilator hub extending from the elongated dilator body, the dilator hub defining an inner cavity having a distal cavity portion and a proximal cavity portion, the dilator hub comprising a dilator sealing surface located on a proximal-facing surface of the dilator hub; and
   a valve element having an open position and a closed position, wherein the valve element is disc shaped, the valve element comprising:
      an arcuate attachment portion configured to be supported by the dilator hub, and
      a sealing portion extending radially inwardly from a side of the inner cavity, the sealing portion comprising a valve sealing surface located, when the valve element is in the closed position, on a distal surface of the sealing portion, the sealing portion being biased toward the closed position with the valve sealing surface positioned against the dilator sealing surface located on the proximal-facing surface of the dilator hub,
      wherein the valve element is configured to inhibit fluid flow between the distal cavity portion and the proximal cavity portion when the valve element is in the closed position,
      wherein the sealing portion of the valve element flexes in a proximal direction, from the closed position to the open position, when a guidewire abuts against and extends past the sealing portion of the valve element, and
      wherein the valve element permits movement of the guidewire through the dilator hub in the proximal direction relative to the dilator.

2. The access device of claim 1, wherein the valve element is at least partially disposed between the distal portion of the inner cavity and the proximal portion of the inner cavity.

3. The access device of claim 1, wherein the valve sealing surface is positioned against the dilator sealing surface to substantially seal the distal cavity portion from the proximal cavity portion when the valve element is in the closed position.

4. The access device of claim 3, wherein at least one of the valve sealing surface and the dilator sealing surface extend around an inner perimeter of the inner cavity.

5. The access device of claim 1, wherein the sealing portion comprises a raised portion.

6. The access device of claim 5, wherein the raised portion comprises a substantially dome-like shape.

7. The access device of claim 1, wherein the valve element comprises a fold line along which the sealing portion and the attachment portion can bend with respect to each other.

8. The access device of claim 1, wherein the valve element comprises a flexible material with properties that reduce the likelihood of cold-setting when held in a flexed position for extended periods of time.

9. The access device of claim 1, wherein movement of the guidewire in a proximal direction relative to the dilator is inhibited when the valve element is in the closed position.

10. The access device of claim 1 further comprising a sheath, the sheath being disposed about the dilator.

11. An access device for placing a medical article within a body space, the access device comprising:
- a dilator comprising:
  - a dilator body, and
  - a dilator hub extending from a proximal end of the dilator body, wherein the dilator hub forms an inner cavity along a longitudinal axis defined by the dilator body and the dilator hub, the dilator hub comprising a dilator sealing surface located on a proximal-facing surface of the dilator hub; and
- a sheath coaxially disposed about the dilator; and
- a valve element being disc shaped, the valve element comprising:
  - an arcuate attachment portion being supported within the inner cavity, and
  - a sealing portion extending into the inner cavity, the sealing portion comprising a valve sealing surface,
  - wherein the valve sealing surface is biased toward a first position against the dilator sealing surface located on the proximal-facing surface of the dilator hub to substantially seal at least a portion of the inner cavity from the dilator body, and
  - wherein the sealing portion is movable in a proximal direction from the first position to a second position when at least a guidewire abuts against and extends past the sealing portion of the valve element and is extended through the inner cavity.

12. The access device of claim 11, wherein the valve element is at least partially disposed between a distal portion of the inner cavity and a proximal portion of the inner cavity.

13. The access device of claim 11, wherein at least one of the valve sealing surface and the dilator sealing surface extend around an inner perimeter of the inner cavity.

14. The access device of claim 11, wherein the sealing portion comprises a raised portion.

15. The access device of claim 14, wherein the raised portion comprises a substantially dome-like shape.

16. The access device of claim 11, wherein the valve element comprises a fold line along which the sealing portion and the attachment portion can bend with respect to each other.

17. The access device of claim 11, wherein the valve element comprises a flexible material with properties that reduce the likelihood of cold-setting when held in a flexed position for extended periods of time.

18. The access device of claim 11, wherein movement of at least one of the needle and the guidewire in a proximal direction relative to the dilator is inhibited when the valve element is in the closed position.

19. The access device of claim 1, wherein the arcuate attachment portion and the valve element are unitary.

20. The access device of claim 11, wherein the arcuate attachment portion and the valve element are unitary.

\* \* \* \* \*